US008247613B2

(12) United States Patent
Williams et al.

(10) Patent No.: US 8,247,613 B2
(45) Date of Patent: Aug. 21, 2012

(54) METHODS AND COMPOSITIONS FOR THE SYNERGISTIC ACTIVATION OF LATENT HIV

(75) Inventors: Samuel A. F. Williams, San Mateo, CA (US); Warner C. Greene, Hillsborough, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 470 days.

(21) Appl. No.: 12/297,034

(22) PCT Filed: Apr. 17, 2007

(86) PCT No.: PCT/US2007/066764
§ 371 (c)(1),
(2), (4) Date: Nov. 25, 2008

(87) PCT Pub. No.: WO2007/121429
PCT Pub. Date: Oct. 25, 2007

(65) Prior Publication Data
US 2010/0168004 A1    Jul. 1, 2010

Related U.S. Application Data

(60) Provisional application No. 60/792,806, filed on Apr. 17, 2006.

(51) Int. Cl.
*C07C 45/00* (2006.01)
*A61K 38/00* (2006.01)
*A61K 38/12* (2006.01)
(52) U.S. Cl. ......... 568/347; 514/3.8; 514/21.1; 514/510
(58) Field of Classification Search .................. None
See application file for complete search history.

(56) References Cited

U.S. PATENT DOCUMENTS
2008/0118494 A1 * 5/2008 Kutsch et al. .............. 424/130.1

OTHER PUBLICATIONS

Korin et al., Journal of Virology, 202, 76(16):8118-8123.*
Bocklandt et al., Antiviral Research, 2003, 59(2):89-98.*
Rosato et al., Cancer Biology & Therapy, 2003, 2(1):30-37.*
Demonte et al., Biochemical Pharmacology, 2004, 68:1231-1238.*
Kulkosky et al., AIDS Research and Human Retroviruses, 2004, 20(5):497-505.*
Williams et al., J. Biol. Chem., 2004, 279(40):42008-42017.*
Kiernan, R., et al., "HIV-1 Tat transcriptional activity is regulated by acetylation" *EMBO Journal*, vol. 18(21), pp. 6106-6118 (1999).
Quivy, V., et al., "Synergistic Activation of Human Immunodeficiency Virus Type 1 Prompter Activity by NF-$_K$B and Inhibitors of Deacetylases: Potential Perspectives for the Development of Therapeutic Strategies," *Journal of Virology*, vol. 76(21), pp. 11091-11103 (Nov. 2002).
Prostratin structural analog—Google Search; http://www.google.com/search?hl=en&q=prostratin+structural+analog&btnG=Search &aq...; Apr. 15, 2011; 2 pages.
12-deoxyphorbol 13-phenylacetate (DPP) structural analog—Google Search; http://www.google.com/search?hl=en&q=12-demphorbol+13-phenylacetate+%28DPP%...; Apr. 15, 2011; 2 pages.
Reuse, Sophie, et al; Synergistic Activation of HIV-1 Expression by Deacetylase Inhibitors and Prostratin: Implications for Treatment of Latent Infection; PLoS ONE; Jun. 2009; vol. 4, Issue 6, e6093; pp. 1-19.

* cited by examiner

*Primary Examiner* — Zachariah Lucas
*Assistant Examiner* — Nicole Kinsey White
(74) *Attorney, Agent, or Firm* — Duane Morris, LLP; Siegfried J. W. Ruppert

(57) ABSTRACT

The present invention provides methods and compositions useful for the elimination of latent HIV reservoirs that persist despite HAART. The methods and compositions overcome this latent barrier by inducing the replication of HIV in latently infected T cells while preventing the spread of the newly produced virions to uninfected cells by providing HAART simultaneously. Compositions of the invention comprise an activator of latent HIV expression, such as prostratin, and an inhibitor of histone deacetylase, such as TSA. A surprising finding of this invention is that the inhibitor of the histone deacetylase synergizes the effect of prostratin thus, allowing administering to a patient a lower, non-toxic dose of prostratin.

34 Claims, 6 Drawing Sheets

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Origin of artificial or unkown sequence: Primer

<400> SEQUENCE: 1
gttagaccag atctgagcct                                                20

<210> SEQ ID NO 2
<211> LENGTH: 20
<212> TYPE: DNA
<213> ORGANISM: Artificial
<220> FEATURE:
<223> OTHER INFORMATION: Origin of artificial or unkown sequence: Primer

<400> SEQUENCE: 2
gtgggttccc tagttagcca                                                20

<210> SEQ ID NO 3
<211> LENGTH: 20
<212> TYPE: DNA
<213> ORGANISM: Artificial
<220> FEATURE:
<223> OTHER INFORMATION: Origin of artificial or unkown sequence: Primer

<400> SEQUENCE: 3
actcgacaga ggagagcaag                                                20

<210> SEQ ID NO 4
<211> LENGTH: 20
<212> TYPE: DNA
<213> ORGANISM: Artificial
<220> FEATURE:
<223> OTHER INFORMATION: Origin of artificial or unkown sequence: Primer

<400> SEQUENCE: 4
```

```
gagtctgact gttctgatga                                              20

<210> SEQ ID NO 5
<211> LENGTH: 18
<212> TYPE: DNA
<213> ORGANISM: Artificial
<220> FEATURE:
<223> OTHER INFORMATION: Origin of artificial or unkown sequence: Primer

<400> SEQUENCE: 5
gtcgacaacg gctccggc                                                18

<210> SEQ ID NO 6
<211> LENGTH: 20
<212> TYPE: DNA
<213> ORGANISM: Artificial
<220> FEATURE:
<223> OTHER INFORMATION: Origin of artificial or unkown sequence: Primer

<400> SEQUENCE: 6
ggtgtggtgc cagattttct                                              20
```

METHODS AND COMPOSITIONS FOR THE SYNERGISTIC ACTIVATION OF LATENT HIV

CROSS-REFERENCES TO RELATED APPLICATIONS

This application is a U.S. National Phase of PCT/US07/066764, filed on Apr. 17, 2007, which claims the benefit of U.S. provisional patent application Ser. No. 60/792,806, filed Apr. 17, 2006, the disclosures of which are incorporated herein in their entirety by reference for all purposes.

STATEMENT AS TO RIGHTS TO INVENTIONS MADE UNDER FEDERALLY SPONSORED RESEARCH OR DEVELOPMENT

This invention was made with Government support of Grant No. A1058708, awarded by the National Institutes of Health. The Government has certain rights in this invention.

FIELD OF THE INVENTION

The present invention generally relates to methods and compositions useful for the elimination of latent HIV reservoirs that persist despite highly active antiretroviral therapy (HAART).

BACKGROUND OF THE INVENTION

Human Immunodeficiency Virus (HIV) is the etiologic agent that is responsible for AIDS, a syndrome characterized by depletion of $CD4^+$ T-lymphocytes and collapse of the immune system. HIV infection is pandemic and HIV-associated diseases have become a world-wide health problem. Upon infection, HIV integrates into the cellular genome of an infected cell. HIV infection then leads to two different scenarios: productive infection and latent infection. Productive infection occurs most frequently and leads to death of the infected cell after release of progeny virus. During latent infection, which is rare, HIV genes are not expressed after proviral integration, resulting in an infected cell that is characterized by transcriptionally silent HIV genes. These fully replication-competent HIV can persist dormant in cells for several years and then become reactivated (Chun et al., 1995, Nature Med 1(12):1284-1290; Chun et al., 1997, Proc Natl Acad Sci USA 94(24):13193-13197; for review, see Bisgrove, 2005, Expert Rev Anti Infect Ther 3(5):805-814).

Current treatments of AIDS typically seek to block one or more steps involved in the production of viral particles. Treatment options involve administration of reverse transcriptase inhibitors, inhibitors of viral protease, fusion, entry, or integration inhibitors in different combinations to block multiple steps in the viral life cycle. This approach, termed highly active antiviral therapy (HAART) has greatly decreased morbidity and mortality in people infected with HIV (Palella et al., 1998, N Engl J Med 338(13):855-860).

However, long-term follow-up studies have shown that HAART alone is not effective in completely eliminating HIV in infected patients. In most cases, upon ceasing HAART a rapid rebound in viremia occurs even after years of successful treatment with undetectable viral loads (Davey et al., 1999, Proc Natl Acad Scxi USA 96(26):15109-15114; Cohen and Fauci, 2001, Adv Intern Med 46:207-246). The rebound in viremia is believed to be due at least in part to the reactivation of latent HIV. Latent forms of HIV are not sensitive to HAART because these drugs (e.g., reverse transcriptase inhibitors, viral protease inhibitors) are only active against actively replicating forms of HIV. Although the frequency of latently-infected cells is only about 0.03-3 infectious units per million resting $CD4^+$ T-cells (Siliciano et al., 2003, Nature Med 9(6):727-728), this latent population of HIV serves as a source of virus for reseeding the infection after discontinuation of HAART. Due to the longevity of this latent HIV reservoir, it is unlikely that HAART alone can ever clear it completely (Siliciano et al., 2003, Nature Med 9(6):727-728).

HIV latency is closely tied to expression of HIV genes, i.e., to HIV transcription, which initiates at a promoter located in the 5' LTR driving transcription of the viral genome. The LTR comprises essentially 4 regions: a negative regulatory element (NRE), an enhancer region, a core promoter and a 5' untranslated region (UTR) (for review, see Bisgrove, 2005, Expert Rev Anti Infect Ther 3(5):805-814). Of particular interest for activation of HIV expression is the enhancer region, which can be subdivided into a distal and proximal region. Several transcription factors bind to these regions. For example, Ets-1 and LEF-1 bind to the distal enhancer region, while the inducible transcription factors nuclear factor-kappa B (NF-κB) and NF-AT bind to and activate HIV transcription from the proximal enhancer.

Select viral proteins are also involved in activation of HIV gene transcription. For example, one of the early proteins expressed from the HIV genome is Tat, a viral transactivator that binds to an RNA recognition element (TAR) present in all viral transcripts and primarily drives high level of HIV expression by enhancing transcriptional elongation in of RNA polymerase II after binding to the HIV LTR.

Recently, several lines of evidence pointed to an inhibitory effect of chromatin on HIV gene expression initiated on the integrated HIV genome. With respect to histone H3, a protein component of a nucleosome (the base unit of chromatin), acetylation or methylation of amino acid residue lysine 9 has been implicated in transcriptionally active or inactive chromatin, respectively. It has been recognized that nucleosomes can negatively regulate gene expression by, e.g., preventing access to the DNA binding sites of transcription factors, thereby reducing or silencing expression of nearby genes (Owen-Hughes and Workman, 1994, Crit Rev Eukaryot Gene Expr 4(4):403-441; Knezeetic and Luse, 1986, Cell 45(1):95-104).

Prior to transcriptional activation, 5 nucleosomes are precisely positioned in the 5' LTR of HIV. Nucleosome nuc-0, encompassing part of the NRE region is separated from nucleosome nuc-1 by a 265 bp nucleosome-free region, containing binding sites for transcription factors C/EBP, LEF-1, NF-κB, NF-AT, Sp1 and the TATA box (Verdin et al., 1993, EMBO J 12(12):4900; Jones and Peterlin, 1994, Annu Rev Biochem 63:717-743). Upon activation, nuc-1 is rapidly remodeled which may relieve a block to HIV gene transcription. Reactivation of HIV latency seems also to involve recruitment of acetyltransferase to the HIV-LTR, followed by acetylation of histones H3 and H4 (Lusic et al., 2003, EMBO J 22(24):6550-6561; Bisgrove, 2005, Expert Rev Anti Infect Ther 3(5):805-814). Thus, chromatin is an integral component of the HIV transcriptional regulatory machinery and modulation thereof are expected to have a direct impact on the expression of HIV genes.

Further, HIV latency may also be explained by integration of the HIV genome into heterochromatin, a transcriptionally repressive form of chromatin, that eventually may become reorganized leading to the activation of latent HGIV-1 expression (Jordan et al., 2003, EMBO J 22(8):1868-1877). Another mechanism underlying HIV latency may be transcriptional interference with a near-by gene (Han et al., 2004, *J Virol* 78(12):6122-6133).

Two strategies have been proposed to overcome the problem that current HAART is unable to completely clear the latent HIV reservoir. The first one can be described as an intensified HAART aiming to prevent even a very low level viral replication (Ramratnam et al., 2004, *J Acquir Immune Defic Syndr* 35(1):33-37). A second approach aims at eliminating the pool of latently infected cells by inducing HIV replication in these cells, while maintaining the patient on HAART to prevent a spreading infection. The latently-infected cells would then be eliminated by the immune system or virus-mediated cell lysis.

In pursuing the second approach, purging the latent HIV pool by activation of viral transcription, several clinical trials have been performed, however, with limited success so far. For example, studies using IL-2 or IL-2 and OKT3 have not shown significant reduction in the latent reservoir and viral rebound continues after cessation of HAART (Chun et al., 1999, *Nat Med* 5:651-655; van Praag et al., 2001, *J Clin Immunol* 21:218-226; Blankson et al., 2002, *Ann Rev Med* 53:557-593). Another potential drug useful for viral purging is IL-7 (Smithgall et al., 1996, *J Immunol* 156(6):2324-2330; Scripture-Adams et al., 2002, *J Virol* 76(24):13077-13082).

Recently, prostratin and the related 12-deoxyphorbol 13-phenylacetate (DPP) were described as promising inducers of latent HIV. Prostratin is a nontumor-promoting phorbol ester initially isolated in screens for inhibitors of HIV replication (Gustafson et al., 1992, *J Med Chem* 35(11):1978-1986). However, further studies indicated that in addition to blocking HIV infection, prostratin treatment, also upregulated HIV transcription from latent proviruses (Kulkosky et al., 2001, Blood 98(10:3006-15; Korin et al., 2002, *J Virol* 76(16):8118-8123; Biancotto et al., 2004, *J Virol* 78(19): 10507-10515).

Prostratin has been reported to antagonize HIV latency by stimulating IKK-dependent phosphorylation and degradation of $I_\kappa B\alpha$, leading to the rapid nuclear translocation of NF-κB binding of this factor to the HIV-LTR enhancer and activation of HIV expression (Williams et al., 2004, *J Biol Chem* 279 (40):42008-42017).

To be clinically useful, activators of latent HIV expression must exhibit relatively low toxicity, permitting patients to withstand treatment with these agents (Perelson et al., 1997, *Nature* 387, 188-191). Although prostratin functions as an activator of latent HIV expression and was observed to lack toxicity when applied for short time courses, in its current dosage regimen, prostratin may not be useful for long-term, multiround treatments in humans. Prostratin was reported to induce substantial growth arrest and cell death if administered in a concentration of >500 nM for more than 2 days (Williams et al., 2004, *J Biol Chem* 279(40):42008-42017). Thus, if prostratin is to be considered as a human therapeutic, it is unlikely that high-dose or protracted treatment will be tolerated. Consequently, either short-term and/or low-dose treatments will probably be the only alternative, since sustained administration or prostrating at high-dose will probably result in dramatically negative side effects (Williams et al., 2004, *J Biol Chem* 279(40):42008-42017). However, no such protocols are available yet.

Histone acetylases and deacetylases play a major role in the control of gene expression. They regulate gene expression by acetylating and deacetylating lysine residues on histones as well as various transcription factors. The balance between the activities of histone acetylases, usually called acetyl transferases (HATs), and deacetylases (HDACs) determines the level of histone acetylation. Acetylated histones are associated with a relaxed, more open form of chromatin and activation of gene transcription, whereas deacetylated chromatin is associated with a more compacted form of chromatin and diminished transcription. Eleven different HDACs have been cloned from vertebrate organisms. A Class I HDACs includes HDAC1, HDAC2, HDAC3, and HDAC8 (Van den Wyngaert et al., 2000, *FEBS Lett* 468:77-83). A Class II HDACs includes HDAC4, HDAC5, HDAC6, HDAC7, HDAC7, HDAC9, and HDAC10 (Kao et al., 2000, *Genes Dev* 14:55-60; Grozinger et al., 1999, *Proc Natl Acad Sci USA*, 96:4868-73; Zhou et al., 2001, *Proc Natl Acad Sci USA*, 98:10572-77; Tong et al., 2002, *Nucleic Acids Res* 30:1114-23). HDAC11 has not been classified yet (Gao et al., 2002, *J Biol Chem* 277:25748-55). All share homology in their catalytic regions.

HDACs have also been implicated in the inhibition of HIV gene expression and thus, may contribute to establishing or maintaining HIV latency (Ylisastigui et al., 2004, *AIDS* 18(8):1101-1108). Further, it has been shown that NF-κB p50-HDAC1 complexes constitutively bind the latent HIV LTR and induce histone deacetylation and repressive changes in chromatin structure of the HIV LTR, changes that impair recruitment of RNA polymerase II and transcriptional initiation (Williams et al., 2006, *EMBO J* 25:139-149).

Thus, histone deacetylase (HDAC) inhibitors are also being considered as an adjuvant with HAART (see, Bisgrove, 2005, *Expert Rev Anti Infect Ther* 3(5):805-814). HDAC inhibitors have the ability to activate a range of HIV subtypes in a variety of different cell types (Van Lint et al., 1996, *EMBO J* 15(5):1112-1120; Quivy et al., 2002, *J Virol* 76(21): 11091-11103). Some HDAC inhibitors are already in clinical use. For example, valproic acid is widely used to reduce epileptic seizures, and phenylbutyrate is used to treat sickle cell anemia and various forms of thalassemia, establishing their safety profile. Recently, it was suggested that the HDAC inhibitor valproic acid may have effects on the activation of latent HIV (Ylisastigui et al., 2004, *AIDS* 18(8):1101-1108).

TSA has been shown to synergize with both ectopically expressed p50/p65 and tumor necrosis factor alpha (TNF-α)/ SFα (TNF)-induced NF-κB to activate the HIV LTR (Quivy et al., 2002, *J Virol* 76(21):11091-11103).

In another study, TSA, has been shown to inhibit HDAC1, leading to the recruitment of RNA polymerase to the latent HIV LTR. This bound polymerase complex, however, remains non-processive, generating only short viral transcripts. Synthesis of full-length viral transcripts can be rescued by the expression of Tat (Williams et al., 2006, *EMBO J* 25:139-149).

Cells latently infected with HIV represent a currently insurmountable barrier to viral eradication in infected patients. New approaches for the elimination of the latently infected HIV cells are urgently needed (see Pomerantz, 2002, *Curr Opin Invest Drugs* 3:1133-1137). Applicants herewith provide compositions and methods useful for the elimination of latent HIV reservoirs that persist despite HAART. The present invention is based, in part, on the Applicants' discovery that HDAC inhibitors, such as trichostatin A and valproic acid, synergize with a small molecule activator of latent HIV expression, such as prostratin, to activate a latent HIV reservoir. This unexpected finding makes possible the use prostratin in methods for eliminating latent HIV reservoirs in a subject at much lower doses than previously possible, thereby avoiding its cytotoxic effects observed upon administering prostratin at higher doses.

BRIEF SUMMARY OF THE INVENTION

This application discloses the surprising finding that activators of latent HIV expression and inhibitors of histone deacetylase synergize to activate latent HIV expression. Thus, the present invention relates to novel compositions and kits comprising such latent HIV expression and inhibitors of histone deacetylase and the uses thereof in methods for activating latent HIV expression, methods for eliminating a latent HIV reservoir, methods for rendering latent HIV sensitive to killing by an immunotoxin, and methods for treating patients infected with latent HIV.

In a first aspect, the present invention provides a method for activating latent HIV expression in a mammalian cell having an integrated HIV genome. In a preferred embodiment of the present invention, this method comprises the steps of (a) contacting the mammalian cell with an amount of an activator of latent HIV expression effective to activate latent HIV expression to a first expression level and (b) contacting the mammalian cell with an amount of an inhibitor of histone deacetylase effective to activate latent HIV expression to a second expression level, wherein the activator of latent HIV expression and the inhibitor of histone deacetylase synergize to generate the second expression level.

Several activators of latent HIV expression can be used to practice this method. For example, an activator of latent HIV expression is selected from the group consisting of prostratin, DPP, and structural analogs thereof. A preferred activator of latent HIV expression is prostratin.

In another embodiment of the present invention, an activator of latent HIV expression is selected from the group consisting of a NF-κB inducer, Tat, NF-AT, and a NF-AT inducer.

Several inhibitors of histone deacetylase can be used to practice this method. For example, an inhibitor of histone deacetylase is selected from the group consisting of trichostatin A, valproic acid, sodium butyrate and structural analogs thereof. A preferred inhibitor of histone deacetylase is trichostatin A. Another preferred inhibitor of histone deacetylase is valproic acid. An additional preferred inhibitor of histone deacetylase is sodium butyrate.

In a preferred embodiment of the present invention, the activator of latent HIV expression is prostratin and the inhibitor of histone deacetylase is trichostatin A.

Another surprising finding of this invention is that combinations of prostratin and inhibitors of HDAC act synergistically in a manner that allows use of much lower dose of prostratin; thus, potentially avoiding its toxicity at full dose. Thus, in a preferred embodiment, the amount of prostratin contacting the mammalian cell is less than 10% of an amount of prostratin that is required to obtain the same second expression level in the absence of trichostatin A.

In a preferred embodiment, the mammalian cell is in a human.

In another preferred embodiment the method of activating latent HIV expression in a mammalian cell that is in a human, comprises the step of administering HAART. Alternatively, the method may comprise the step of administering an immunotoxin.

Methods of the present invention may also comprise the step of determining the second expression level, for example, by determining HIV RNA expression or by determining HIV polypeptide expression.

In another preferred embodiment, the method of activating latent HIV expression comprises the step of administering Tat.

All mammalian cells into which HIV integrates can be used to practice the methods of the present invention. In a preferred embodiment, the mammalian cell is a resting lymphoid mononuclear cell, preferably a CD4+ T cell. Preferred is also a CD4+ macrophage. The mammalian cell may also be a myeloid mononuclear cell, preferably a peripheral blood mononuclear cell. Another preferred mammalian cell is a tissue macrophage.

In a further aspect, the present invention provides pharmaceutical compositions. A preferred pharmaceutical composition for eliminating a latent HIV reservoir in a mammalian cell comprises (i) an activator of latent HIV expression, (ii) an inhibitor of histone deacetylase, and (iii) a pharmaceutically acceptable carrier.

In another aspect, the present invention provides for the use of an activator of latent HIV expression and an inhibitor of histone deacetylase in the manufacture of a medicament, which can be used to eliminate a latent HIV reservoir in a mammalian cell.

In yet another aspect, the present invention provides kits. Kits of the invention can be used to practice the methods of the invention. A kit for eliminating a latent HIV reservoir in a mammalian cell comprises (i) a first container containing an activator of latent HIV expression, (ii) a second container containing an inhibitor of histone deacetylase, and (iii) an instruction for using the activator of latent HIV expression and the inhibitor of histone deacetylase for eliminating the latent HIV reservoirs in the cell.

DETAILED DESCRIPTION OF THE INVENTION

I. Definitions

Figure 1A:
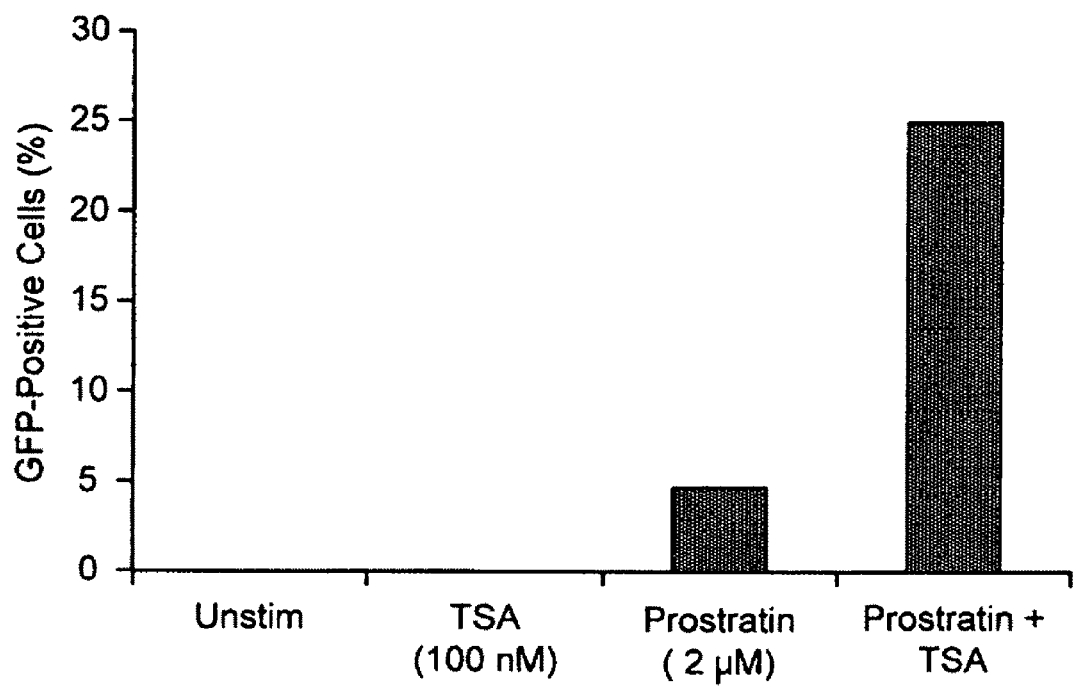
FIG. 1 shows that TSA synergizes with prostratin to activate latent HIV expression. A. Expression of latent HIV expression is induced in J-Lat 6.3 cells. B. Expression of latent HIV expression is induced and in J-Lat 8.4 cells. TSA was used at a concentration of 100 nM and prostratin at a concentration of 2 µM, respectively. C. Low concentrations of prostratin are sufficient to activate latent HIV expression when coadministered with TSA. TSA and prostratin were used at the concentrations indicated. Activation of latent HIV expression was determined as % of GFP-positive cells. Unstim, unstimulated. Details are described in Example 2.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, "activator of latent HIV expression" means any compound that (i) can stimulate proviral latent DNA integrated into the genome of a host to begin transcription initiation, transcription elongation or replication and production of infectious virus and/or cell surface antigens, such as gp120 and/or gp41; and (ii) has a synergistic effect when co-administered with an HDAC inhibitor.

As used herein, "biological sample" means a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure expression level of a polynucleotide or polypeptide. Numerous types of biological samples can be used in the present invention, including, but not limited to, a tissue biopsy or a blood sample. As used herein, a "tissue biopsy" refers to an amount of tissue removed from an animal, preferably a human, for diagnostic analysis. "Tissue biopsy" can refer to any type of biopsy, such as needle biopsy, fine needle biopsy, surgical biopsy, etc. A "biological sample" encompasses samples that have been manipulated in any way after their procurement, such as by treatment with reagents; washed; or enrichment for certain cell populations, such as CD4$^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

As used herein, "providing a biological sample" means to obtain a biological sample for use in methods described in this invention. Most often, this will be done by removing a sample of cells from a subject, but can also be accomplished by using previously isolated cells (e.g., isolated by another person, at another time, and/or for another purpose), or by performing the methods of the invention in vivo. Archival tissues, having treatment or outcome history, will be particularly useful.

As used herein, "effective amount", "effective dose", "sufficient amount", "amount effective to", "therapeutically effective amount" or grammatical equivalents thereof mean a dosage sufficient to produce a desired result, to ameliorate, or in some manner, reduce a symptom or stop or reverse progression of a condition. In some embodiments, the desired result is an increase in latent HIV expression. In other embodiments, the desired result is the complete eradication of a latent HIV reservoir. Amelioration of a symptom of a particular condition by administration of a pharmaceutical composition described herein refers to any lessening, whether permanent or temporary, lasting or transit that can be associated with the administration of the pharmaceutical composition. An "effective amount" can be administered in vivo and in vitro.

The terms "eliminating", "eradicating" or "purging" are used interchangeably.

The terms "full length viral mRNA" or "full length transcript" are used interchangeably and mean polyadenylated viral mRNA. The TAR sequence forms the leader sequence of the full length viral mRNA. In the presence of Tat, viral RNA is elongated beyond the TAR leader sequence and is polyadenylated into full length viral mRNA. Full length viral mRNA includes both spliced and unspliced mRNA.

As used herein, "HAART" refers to a treatment for HIV infection which is a cocktail of anti-viral drugs known as Highly Active Anti-Retroviral Therapy. HAART includes two reverse transcriptase inhibitors and a protease inhibitor. HAART reduces the viral load in many patients to levels below the current limits of detection, but the rapid mutation rate of this virus limits the efficacy of this therapy (Perrin and Telenti, 1998, *Science* 280:1871-1873). In addition, HAART is ineffective in treating latent HIV infection.

As used herein "HDAC" means histone deacetylase.

As used herein, "HDAC inhibitor" or "inhibitor of HDAC" means any compound that (i) inhibits the activity of a histone deacetylase (HDAC) and (ii) has a synergistic effect on an activator of latent HIV expression, wherein the synergistic effect results in an increase of transcription initiation or transcription elongation from an HIV genome integrated into the genome of a host, compared to the transcription initiation or transcription elongation obtained with the activator of latent HIV expression alone.

As used herein, "HIV" is used herein to refer to the human immunodeficiency virus. It is recognized that the HIV virus is an example of a hyper-mutable retrovirus, having diverged into two major subtypes (HIV-1 and HIV-2), each of which has many subtypes. However, compounds of the present invention can activate the LTR promoters from all HIV and other retroviruses which are similar to HIV-1 in the LTR region. Thus, the term "HIV" used herein, unless otherwise indicated, refers to any retrovirus which is regulated by an LTR promoter or LTR promoter homologue which shows inhibition of the LTR promoter or LTR promoter homologue by calcium response modifiers.

The terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by an immunodeficiency virus.

As used herein, "individual," "host," "subject," or "patient," to be treated for a condition or disease by a subject method means either a human or non-human animal in need of treatment for a condition or disease. A preferred condition is a condition affected by or caused by latent HIV infection.

As used herein, the term "isomers" refers to compounds of the present invention that possess asymmetric carbon atoms (optical centers) or double bonds. The racemates, diastereomers, geometric isomers and individual isomers are all intended to be encompassed within the scope of the present invention.

As used herein, "in vitro" means outside the body of the organism from which a cell or cells is obtained or from which a cell line is isolated.

As used herein, "in vivo" means within the body of the organism from which a cell or cells is obtained or from which a cell line is isolated.

As used herein, a "label" or a "detectable moiety" means a composition detectable by spectroscopic, photochemical, biochemical, immunochemical, chemical, or other physical means. For example, useful labels include $^3$H, $^{125}$I, $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a small molecule compound. A label may be incorporated into a small molecule compound, such as a prostratin, DPP, TSA, or valproic acid at any position.

As used herein, "latency", "latent", "latently infected reservoir" or grammatical equivalents thereof refer to the integration of a viral genome or a integration of a partial viral genome within a host cell genome further characterized by (i) the undetectable level of non-spliced viral RNA (<500 copies RNA/ml by a commonly used PCR assay; Chun et al., 1997, *Proc Natl Acad Sci USA*, 94:13193-13197); (ii) absence of detectable viral production; or (iii) only about $10^5$ to $10^6$ latently infected CD4 memory T cells in a subject (Williams et al., 2004, *J Biol Chem* 279(40):42008-42017). "Latency" also means a concept describing (i) an asymptomatic clinical condition; (ii) the state of viral activity within a population of cells, or (iii) the down-regulation or absence of gene expression within an infected cell.

As used herein, "level of a mRNA" in a biological sample refers to the amount of mRNA transcribed from a gene that is present in a cell or a biological sample. The mRNA generally encodes a functional protein, although mutations may be present that alter or eliminate the function of the encoded protein. A "level of mRNA" need not be quantified, but can simply be detected, e.g., a subjective, visual detection by a human, with or without comparison to a level from a control sample or a level expected of a control sample. A preferred mRNA is a HIV mRNA.

As used herein, "level of a polypeptide" in a biological sample refers to the amount of polypeptide translated from a mRNA that is present in a cell or biological sample. The polypeptide may or may not have protein activity. A "level of a polypeptide" need not be quantified, but can simply be detected, e.g., a subjective, visual detection by a human, with or without comparison to a level from a control sample or a level expected of a control sample. A preferred polypeptide is an HIV polypeptide, such as GP 120, reverse transcriptase, Gag polypeptide or its protease-processed products.

As used herein, "LTR" means the Long Terminal Repeat, a sequence repeated at the 5' and 3' ends of an HIV genome, which consists of an enhancer and a promoter region for gene expression, a RNA transcription start site, and an untranslated RNA sequence.

As used herein, "non-processive transcription" means initiation with inefficient elongation (transcription complexes pause and drop of the DNA) leading to an abundance of short, non-polyadenylated RNA and only rarely in elongated full length mRNAs. "Processive transcription" means efficient elongation of transcripts leading to high levels of polyadenylated mRNA.

As used herein, "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

As used herein, "reactivated," or grammatical equivalents thereof, in the context of in vivo reactivated HIV, refers to an HIV that, after a period of latency, becomes transcriptionally active, and in many instances forms infectious viral particles. The term "reactivated," as used herein in the context of in vitro reactivated HIV in a subject cell, refers to an HIV (e.g., a recombinant HIV) that, after a period of latency, becomes transcriptionally active, i.e., a functional Tat protein mediates transcription from a functional HIV promoter (e.g., a long terminal repeat promoter).

As used herein, the term "salts" refers to salts of the active compounds of the present invention, such as activators of latent HIV expression or HDAC inhibitors, which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "solvate" refers to compounds of the present invention that are complexed to a solvent. Solvents that can form solvates with the compounds of the present invention include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

As used herein, "TAR" means the Trans-Activating Response element which is the target for Tat binding. The TAR region is the first 59-61 nt of the nascent RNA, the leader sequence positioned immediately 3' of the transcription start site. It forms a stem-loop structure.

As used herein, "Tat" means the virally encoded trans-activating protein which functions as an elongation factor. Tat is essential for viral replication as the key viral element for increasing HIV gene expression.

As used herein, "transcription competent" in the context of transcription-competent latent HIV, refers to a latent HIV (including latent HIV-based retroviral vectors) that encodes functional Tat and has a functional TAR site in the LTR.

As used herein, the terms "treat", "treating", and "treatment" include: (1) preventing a condition or disease, i.e. causing the clinical symptoms of the condition or disease not to develop in a subject that may be predisposed to the condition or disease but does not yet experience any symptoms of the condition or disease; (2) inhibiting the condition or disease, i.e. arresting or reducing the development of the condition or disease or its clinical symptoms; or (3) relieving the condition or disease, i.e. causing regression of the condition or disease or its clinical symptoms. These terms encompass also prophylaxis, therapy and cure. Treatment means any manner in which the symptoms or pathology of a condition, disorder, or disease are ameliorated or otherwise beneficially altered. Preferably, the subject in need of such treatment is a mammal, more preferable a human.

II. Small Molecule Compositions

Applicants describe herein novel approaches for eliminating a latent HIV reservoir, wherein expression of the latent HIV is activated by the synergistic action of an activator of latent HIV expression and an HDAC inhibitor. As described herein, it is an objective of the present invention to provide activators of latent HIV expression and HDAC inhibitors useful to practice the methods of the present invention. Thus, the present invention provides compositions and methods that are useful in a wide range of methods. These methods include, but are not limited to, a method for activation of latent HIV expression, a method for eliminating a latent HIV reservoir, a method for increasing latent HIV gene expression, a method for rendering a latent HIV sensitive to killing by an immunotoxin or HAART; a method for treating HIV latency; and a method for increasing the activity of an LTR promoter in a T cell. This invention discloses the surprising finding that inhibitors of histone deacetylase (HDAC) synergize the effect of an activator of latent HIV expression. The compounds and composition disclosed herein can be used in either method described herein.

The inhibitors of histone deacetylase and the activators of latent HIV expression contemplated for use in the methods of the present invention will be described in detail below. In addition, the salts, hydrates, solvates, isomers, prodrugs, and structural analogs of these compounds d also contemplated.

A. Inhibitors of Histone Deacetylase

Figure 7:
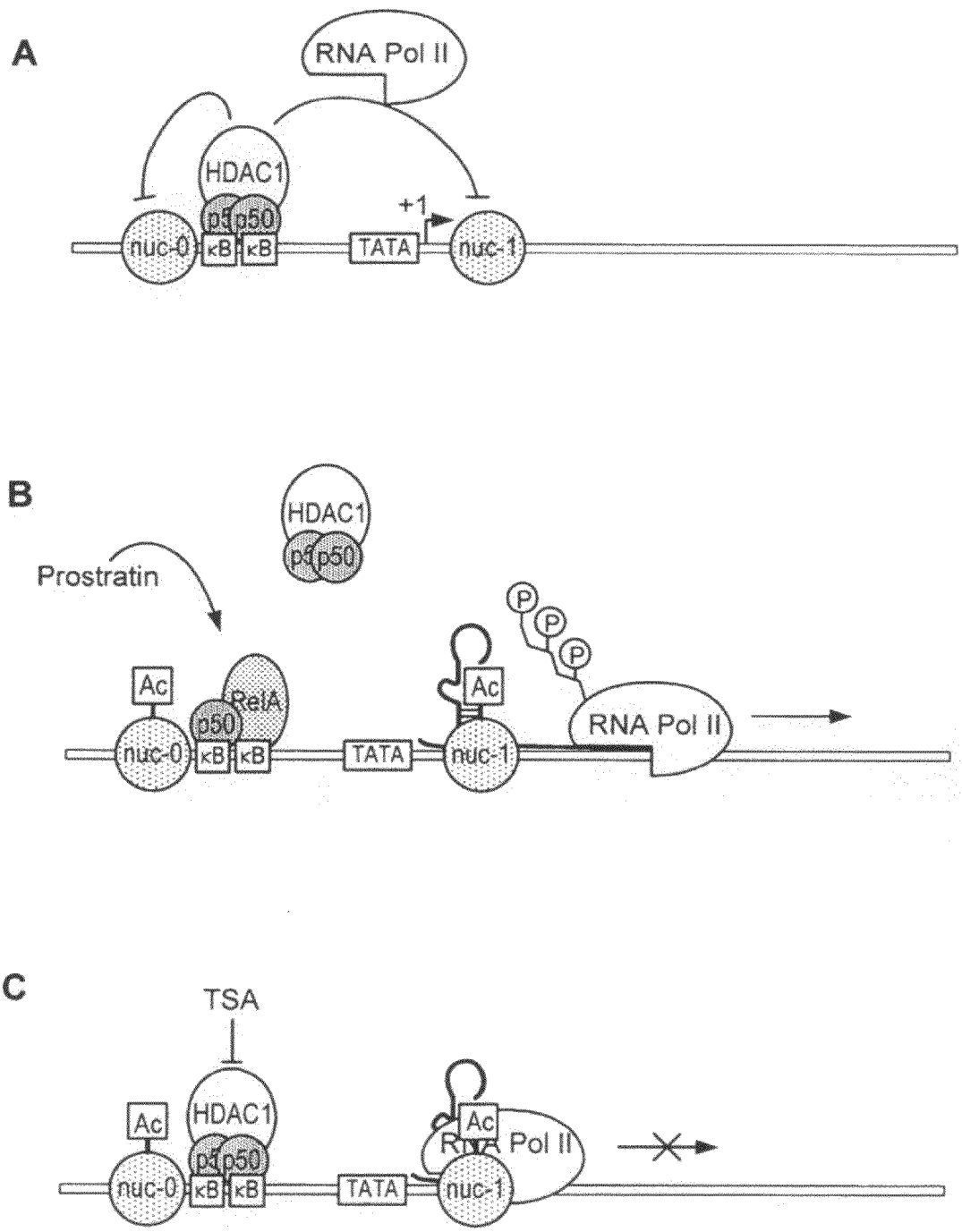
FIG. 7 shows a model for activation of latent HIV expression. A. Latent HIV status. Histone deacetylase 1 (HDAC1) binds to NF-κB p50 homodimer which binds to the proximal enhancer region within the 5' HIV LTR. HDAC1 is at least one of the HDACs that is recruited to the HIV LTR and removes acetyl groups from histones. Nuc-1 represents a repressive nucleosome preventing recruiting RNA polymerase II. B. Activation of latent HIV expression. Prostratin leads to the nuclear translocation of NF-κB (shown here as p50/RelA heterodimer complex), binding to the proximal enhancer region and displacing the HDAC1/p50/p50 complex. Following a remodeling of the nucleosomes involving acetylation (Ac), RNA polymerase II is recruited to the TATA box, initiates transcription and elongates HIV transcripts. C. TSA inhibits HDAC1, leading to the recruitment of RNA polymerase to the latent HIV LTR. This bound polymerase complex, however, remains non-processive, generating only short viral transcripts. (see, Williams et al., 2006, *EMBO J* 25:139-149). The following abbreviations are used: Nuc-0, nuc-1, nucleosomes flanking the HIV LTR region; HDAC1, histone deacetylase 1; p50, subunit of NF-κB dimer; RelA, p65 subunit of NF-κB protein; $_κ$B, binding site for NF-κB dimer and p50/RelA proteins in the HIV LTR enhancer region; TATA, binding site of transcription factors initiating transcription at position +1; RNA Pol II, RNA polymerase II, a complex of transcription factors capable of initiating transcription initiation; Ac, acetylation of a Histone; P, indicating chain elongation of an RNA transcript; TSA, trichostatin A. A RNA hairpin loop (TAR) formed at the 5' termini of nascent HIV transcripts is indicated. Tat, when present binds to TAR and upregulates HIV gene expression.

As described herein, one explanation for the low level of HIV transcription during postintegration latency may be the presence of repressive nucleosomes (see FIG. 7A) and the presence of histone deacetylases (HDAC) contributing to transcription silencing or repression. Thus, in a preferred embodiment, a composition comprises an inhibitor of HDAC.

In accordance with the preceding embodiments, the histone deacetylase inhibitor may be any molecule that effects a reduction in the activity of a histone deacetylase. This includes proteins, peptides, DNA molecules (including antisense), RNA molecules (including RNAi and antisense) and small molecules.

The small molecule HDAC inhibitors include, but are not limited to, trichostatin A, butyric acid, phenylbutyrate, phenylacetate, trapoxin B (porphrin derivative, $C_{33}H_{30}N_4O_6$, Kijima et al., 1993, *J Biol Chem* 268(30):22429-35), MS 275-27 (benzamide derivative, $C_{21}H_{20}N_4O_3$), hydroximates (e.g., suberoylanilide hydroxamic acid [SAHA, hydroxamic acid, $C_{14}H_{20}N_2O_3$, Butler et al., 2000, *Cancer Res* 60:5165-5170; Marks et al., *Clin Cancer Res* 7:759-760; Richon et al., 1998, *Proc Natl Acad Sci USA,* 95(6):3003-7]; azelaic bishydroxamic acid [ABHA, Parsons et al., 2002, *Biochem Pharmacol* 53:1719-1724]; suberic bishydroxamic acid [SBHA]; m-carboxycinnamic acid bis-hydroxamide [CBHA, hydroxamic acid, $C_{14}H_{20}N_2O_3$, Coffey et al., 2001, *Cancer Res* 61:3591-3594]), depudecin (fungal metabolite, $C_{11}H_{16}O_4$), oxamflatin (aromatic sulfonamide, $C_{18}H_{14}N_2O_4S_1$), apicidin (cyclo(N-O-methyl-L-tryptophanyl-L-isoleucine-D-pipecolinyl-1-2-amino-8-oxodecanoyl, cyclopeptide $C_{29}H_{38}N_5O_6$), Scriptaid (hydroxamic acid, $C_{18}H_{12}N_2O_4$), pyroxamide (suberoyl-3-aminopyridineamide hydroxyamic acid, $C_{13}H_{20}N_3O_3$, Butler et al., 2001, *Clin Cancer Res* 7:962-970), 2-amino-8-oxo-9,10-epoxy-decanoyl (AEO, ketone, $C_{10}H_{17}NO_3$), 3-(4-aroyl-1H-pyrrol-2-yl)-N-hydroxy-2-propenamide (propenamide, $C_{14}H_{12}N_2O_3$), CI-994 (N-acetyldinaline; Kraker et al., 2003, *Mol Cancer Ther* 2(4): 401-8; el-Beltagi et al., 1993, *Cancer Res* 53:3008-14; commercially available from Pfizer), CHAP1 (trichostatin A+trapoxinB, hydroxamic/porphyrin derivatives), CHAP31 (Furumai et al., 2001, *Proc Natl Acad Sci USA* 98:97-92; Komatsu et al., 2001, *Cancer Res* 61(11):4459-66; commercially available from Japan Energy Corporation); CHAP50 (Furumai et al., 2001, *Proc Natl Acad Sci USA* 98:97-92,; Komatsu et al., 2001, *Cancer Res* 61(11):4459-66; commercially available from Japan Energy Corporation), MS-275 (Suzuki et al., 1999, *J Med Chem* 42:3001-3; commercially available from Mitsui Pharmaceuticals, Inc.), M344 (Jung et al., 1999, *J Med Chem* 42:4669-4679), LAQ-824 (Catley et al., 2003, *Blood* 102(7):2615-22), FR901228 (cyclopeptide, $C_{24}H_{36}N_4O_6S_2$), FK228 (depsipeptide, Darkin-Rattray et al., 1996, *Proc Natl Acad Sci USA* 93(23):13143-7) and HC-toxin (Brosch et al., 1995, *Plant Cell* (11):1941-50). Additionally, the following references describe histone deacetylase inhibitors which may be selected for use in the current invention: AU 9,013,101; AU 9,013,201; AU 9,013,401; AU 6,794,700; EP 1,233,958; EP 1,208,086; EP 1,174,438; EP 1,173,562; EP 1,170,008; EP 1,123,111; JP 2001/348340; U.S. 2002/103192; U.S. 2002/65282; U.S. 2002/61860; WO 02/51842; WO 02/50285; WO 02/46144; WO 02/46129; WO 02/30879; WO 02/26703; WO 02/26696; WO 01/70675; WO 01/42437; WO 01/38322; WO 01/18045; WO 01/14581; Furumai et al. 2002, *Cancer Res* 62:4916-21; Hinnebusch et al., 2002, J Nutr 132:1012-7; Mai et al., 2002, *J Med Chem* 45:1778-1784; Vigushin et al., 2002, *Anticancer Drugs* 13:1-13; Gottlicher et al., 2001, *EMBO J* 20:6969-78; Jung, 2001, *Curr Med Chem* 8:1505-11; Komatsu et al., 2001, *Cancer Res* 61:4459-66; Su et al., 2000, 60:3137-3142.

This invention discloses that histone deacetylase inhibitors synergize with an activator of latent HIV expression, such as prostratin, to activate latent HIV expression. Further, this invention discloses that histone deacetylase inhibitors block or reduce prostratin-induced cell death.

1. Trichostatin A

In a preferred embodiment of the present invention, a histone deacetylase inhibitor is trichostatin A (TSA). TSA is a hydroxamic acid, [R-(E,E)]-7-[4-(Dimethylamino)phenyl]-N-hydroxy-4,6-dimethyl-7-oxo-2,4-heptadienamide). It his commercially available (BIOMOL Research Labs, Inc., Plymouth Meeting, Pa. and Wako Pure Chemical Industries, Ltd).

2. Valproic Acid

Another preferred histone deacetylase inhibitor is valproic acid (VpA). VpA is 2-propylpentanoic acid, Valproic acid, valproate sodium, and divalproex belong to a group of medicines called anticonvulsants that are currently marketed to control certain types of seizures in the treatment of epilepsy. Valproic acid is marketed as "Depakene" (Abbott Laboratories). Divalproex is marketed as "Depakote" (Sanofi-Aventis for UK; Abbott Laboratories for U.S.) and as "Epival" (Abbott Laboratories for Canada). Valproate sodium is marketed as "Depacxon."

Divalproex and valproate sodium form valproic acid in the body. Divalproex is available for oral administration as delayed-release capsules (in U.S., United States of America) and delayed-release tablets (in U.S. and Canada). VpA is also available for oral administration as capsules (U.S.) and as syrup (in U.S. and Canada). Valproate sodium is used for parenteral administration (injection) in the U.S.

Here, Applicants describe a novel use of VpA, Divalproex and valproate sodium in the methods of the present invention.

Thus, in a preferred embodiment of a method of the present invention, Divalproex or valproate sodium is coadministered with an activator of latent HIV activation.

VpA is rapidly absorbed after oral administration. Peak serum levels occur approximately 1 to 4 hours after a single oral dose. The serum half-life of VpA is typically in the range of 6-16 hours.

3. Butyric Acid

Another preferred HDAC inhibitor is butyric acid, preferably sodium butyrate. Preferably, butyric acid is in the form of arginine butyrate or isobutyramide. Butyric acid is one of many naturally-occurring short-chain fatty acids that are generated in the small and large bowel by metabolism of carbohydrates. Butyrate is a four-carbon fatty acid with weakly acidic properties, and is rapidly absorbed and metabolized. Butyrates have shown significant anti-tumor effects. Sodium butyrate (NaB) has been used clinically in patients with acute myelogenous leukemias and there has now been extensive experience with arginine butyrate, a salt of butyrate, in clinical studies for the treatment of β-hemoglobinopathies, and more recently with refractory solid neoplasms (Foss et al., 1994, *Proc. ASCO* 13:162; Sanders et al., *Proc. ASCO*, 1995).

In another preferred embodiment of the present invention, a histone deacetylase inhibitor is a small interfering RNA (siRNA), for example, a si/shRNA directed against HDAC1, 2, 3, 4, 5, 6, 7, 8, 9, 10, or 11.

The activity of an HDAC inhibitor may be measured as described herein. An HDAC inhibitor may have an inhibitory effect against at least one class I HDAC or against at least one class II HDAC or against at least one class I and at least one class II HDAC.

B. Activators of Latent HIV Expression

Several activators of latent HIV expression can be used in the compositions and methods of the present invention. A preferred composition of the invention comprises a small molecule that activates latent HIV expression, such as prostratin, DPP and some NF-κB inducers. In another embodiment, an activator of latent HIV expression is a polypeptide, such as NF-κB, Tat, or NF-AT.

1. Prostratin

A preferred activator of latent HIV expression is prostratin (12-deoxyphorbol 13-acetate). Prostratin is a relatively polar, non-tumorigenic phorbol ester, identified in extracts of *Homalanthus nutans*, a tropical plant used in Samoan herbal medicine primarily for the treatment of jaundice) and stimulates protein kinase C (PKC; Gustafson et al., 1992, *J Med Chem* 35(11):1978-86).

2. DPP

Another preferred activator of latent HIV expression is 12-deoxyphorbol 13-phenylacetate (DPP; Bocklandt et al., 2003, *Antiviral Res* 59(2):89-98; Kulkjosky et al., 2004, *AIDS Res Hum Retroviruses* 20(5):497-505). DPP has been reported to be 20-40 fold more potent than prostratin, probably due to its more lipophilic side chain structure (Bocklandt et al., 2003, *Antiviral Res* 59(2):89-98).

3. Pro-Dugs and Derivatives

This invention also contemplates for use in the methods, kits and compositions described herein the use of natural pro-drugs of prostratin, which may be identified in extracts from *Homalanthus nutans* using methods known in the art and assays described herein.

Further, this invention also contemplates for use in the methods, kits and compositions described herein derivatives of prostratin and DPP, which may be prepared chemically using methods known in the art and tested for synergism with n HDAC inhibitor, for example, by employing assays described herein.

4. NF-κB Inducers

NF-κB and transcription factor Sp1 have been demonstrated to be key factors in stimulating replication of HIV, since viruses lacking binding sites for either transcription factor display attenuated replicative capacity (Leonard et al., 1989, *J Virol* 63:4919-4924). It has been proposed that the absence of NF-κB in the nuclei of latently infected CD4 lymphocytes could play a key role in promoting or maintaining proviral latency in this lymphocyte subset (Williams et al., 2004, *J Biol Chem* 279(40):42008-42017). As described herein, one explanation for the low level of HIV transcription during postintegration latency may be the absence of the inducible transcription factor NF-κB. Thus, in certain embodiments of the present invention, an NF-κB inducer is co-administered with an HDAC inhibitor.

a) Prostratin

As reported by Williams et al. and by Rullas et al., prostratin antagonizes HIV latency by activating NF-κB (see FIG. 7B; Williams et al., 2004, *J Biol Chem* 279(40):42008-42017; Rullas et al., 2004, *Antivir Ther* 9(4):545-54). Thus, in a preferred embodiment of the present invention, a NF-κB inducer is prostratin. Another preferred NF-κB inducer is prostratin succinate sodium (unpublished studies from S Williams).

b) TNF-alpha

Another preferred NF-κB inducer is TNF-alpha (TNFα; Osborn et al., 1989, *Proc Natl Acad Sci USA* 86(7):2336-40; Israel et al., 1989, *EMBO J* 86(7):2336-40).

c) PMA

Another preferred NF-κB inducer, particularly for in vitro assays, is 4-α-phorbol 12-myristate 13-acetate (PMA; Sen et al., 1986, *Cell* 47(6):921-8). Due to its tumor-inducing activity, the in vivo use of PMA may be limited, particularly in humans.

d) Other NF-κB Inducers

Several other NF-κB inducers can be used to practice the methods of the present invention. Thus, other preferred NF-κB inducers include, but are not limited to TNF-beta (Messer et al., 1990, *Cytokine* 2(6):389-97); IL-1beta (Osborn et al., 1989 *Proc Natl Acad Sci USA* 86(7):2336-40); lipopolysaccharide (Sen et al., 1986 *Cell* 47(6):921-8); UV-light (Stein et al., 1989, *Mol Cell Biol* 9(11):5169-81); CD3 antibodies (Tong-Starkesen et al., 1989, *J Immunol* 142(2):702-7); CD3/CD28 antibodies in conjunction (Tong-Starkesen et al., 1989 *J Immunol* 142(2):702-7); Etopiside (Bessho et al., 1999, *Anticancer Res* 19(1B):693-8); Daunorubicin (Wang et al., 1996, *Science* 274(5288):784-7); hydrogen peroxide (Shreck et al., 1991, *EMBO J* 10(8):2247-58); Nocodazole (Rosette et al., 1995, *J Cell Biol* 128(6):1111-9); LIGHT (Zou et al., 2005, *J Cell Physiol* 205(3):437-43); bleomycin (Ishii et al., 2002, *Toxicol Appl Pharmacol* 184(2):88-97); camptothecin (Piret et al., 1996 *Nucleic Acids Res* 24(21):4242-8); cisplatin (Nie et al., 1998, *Mol Pharmacol* 53(4):663-9); celecoxib (Kim et al., 2004, *J Cancer Res Clin Oncol* 130(9):551-60); ciprofibrate (Li et al., 1996, *Carcinogenesis* 17(11):2305-9); cyloprodigiosin (Teshima et al., 2004, *Nitric Oxide* 11(1):9-16); dacarbazine (Lev et al., 2003, *Mol Cancer Ther* 2(8):753-63); Daio-Orengedeokuto (Cho et al., 2004, *Can J Physiol Pharmacol* 82(6):380-6); daunomycin (Das et al., 1997, *J Biol Chem* 272(23):14914-20); diazoxide (Eliseev et al., 2004, *J Biol Chem* 279(45):46748-54); diclofenac (Cho et al., 2005, *FEBS Lett* 579(20):4213-8); 5,6-dimethylxanthenone-4-acetic acid (Ching et al., 1999, *Biochem Pharmacol* 58(7): 1173-81); flavone-8-acetic acid (Ching et al., 1999, *Biochem Pharmacol* 58(7):1173-81); haloperidol (Post et al., 1998, *J Neurosci* 18(20):8236-46); imiquimod (Schon et al., 2006, *Expert Opin Ther Targets* 10(1):69-76); isochamaejasmin (Tian et al., 2005, *Mol Pharmacol* 68(6):1534-42); Kunbi-Boshin-Hangam-Tang (Koo et al., 2001, *Immunopharmacol Immunotoxicol* 23(2):175-86); lithium (Nemeth et al., 2002, *J Biol Chem* 277(10):7713-9); mitoxantrone (Boland et al., 2000, *J Biol Chem* 275(33):25231-8); morphine (Yin et al., *J Neuroimmunol* 2006 Mar. 7 [Epub ahead of print]); nipradilol (Ando et al., 2005, *Exp Eye Res* 80(4):501-7); norepinephrine (Minneman et al., 2000, *J Neurochem* 74(6):2392-400); nystatin (Ogawa et al., 2006, *J Invest Dermatol* 126(2):349-53); oltipraz (Nho et al., 2004, *J Biol Chem* 279(25):26019-27); protocatechuic acid (Zhou-Stache et al., 2002, *Med Biol Eng Comput* 40(6):698-703); SN38 (metabolite of CPT-11; Kishida et al., 2005, *Cancer Chemother Pharmacol* 55(4): 393-403); tamoxifen (Ferline et al., 1999, *Br J Cancer* 79(2): 257-63); Taxol (Paclitaxel; Hwang et al., 1995, *Cancer Biochem Biophys* 14(4):265-72); vinblastine (Rosette et al., 1995, *J Cell Biol* 128(6):1111-9); vincristine (Das et al., 1997, *J Biol Chem* 272(23):14914-20); and WR1065 (Grdina et al., 2002, *Mil Med* 167(2 Suppl):51-3).

5. Tat

As described herein, one explanation for the low level of HIV transcription during postintegration latency may be the absence of the inducible transcription factor Tat. TSA has been shown to inhibit HDAC, leading to the recruitment of RNA polymerase to the latent HIV LTR. This bound polymerase complex, however, remains non-processive, generating only short viral transcripts (see FIG. 7 C). Synthesis of full-length viral transcripts can be rescued by the viral transactivator protein Tat (Williams et al., 2006, *EMBO J* 25:139-149). Thus, in certain embodiments of the present invention, a method comprises the step of administering Tat to a cell or to a subject. In another embodiment of the present invention, a composition comprises Tat.

In one embodiment of the invention, the Tat is a recombinant Tat. The basic molecular biological techniques employed in generating a recombinant Tat, i.e., methods such as DNA and plasmid isolation, restriction enzyme digestion, DNA ligation, purification and characterization of DNAs by polyacrylamide and agarose gel electrophoresis, labeling and hybridization of DNAs, Southern blotting, transformation, maintenance and growth of bacterial strains, protein expression and protein purification, and other general techniques are all well known in the literature. Specifically, the general techniques of molecular biology are described in "Molecular Cloning A Laboratory Manual" by Sambrook, J., Fritsch, E. F., and Maniatis, T. published by Cold Spring Harbor Laboratory Press, 2nd edition, 1989, or "A Practical Guide to Molecular Cloning" by Bernard Perbal published by John Wiley & Sons, New York, 1984.

Generally, the DNA encoding Tat is cloned into an expression vector and transformed into a suitable host cell, which expresses the recombinant Tat. The recombinant Tat may then be purified using methods known to the skilled artisan.

Alternatively, a composition of the present invention comprises a plasmid construct encoding Tat.

6. NF-AT

As described herein, one explanation for the low level of HIV transcription during postintegration latency may be the absence of the inducible transcription factor NF-AT (nuclear factor of activated T cells). Activation of latent HIV gene expression by NF-AT seems to be independent from the NF-κB activation pathway (Brooks et al., 2003, *Proc Natl Acad Sci USA,* 100(22):12955-12960). Thus, in certain embodiments of the present invention, a method comprises the step of administering NF-AT to a cell or to a subject. In another embodiment of the present invention, a composition comprises NF-AT. In yet another embodiment, a method comprises the step of administering a small a NF-AT inducer. In another preferred embodiment of the present invention, a composition comprises a NF-AT inducer which induces NF-AT in a cell.

7. Additional Activators of Latent HIV Expression

Additional activators of latent HIV expression can be identified routinely. For example, the J-Lat cell lines described herein and other established cell lines harboring latent HIV, such as OM-10.1, U1, or Jurkat cells, can be treated with various amount of an agent, e.g., an agent from a combinatorial chemical library to determine effective doses and conditions for obtaining productive HIV infection.

C. Testing Inhibitors of Histone Deacetylase and Activators of Latent HIV Expression The small molecules described herein and agents derived therefrom through routine chemical manipulations that are useful for purging a latent HIV reservoir can be tested for their potential to activate latent HIV expression using the assays described herein. Other useful assays have been described in the art. For example, the small molecules described herein can be tested for induction of HIV expression in patient peripheral blood mononuclear cell (PBMC) cultures obtained from HIV infected individuals (e.g., Kulkosky et al., 2001, *Blood* 98(10):3006-15). Alternatively, the activation potential of the small molecules can be evaluated testing for reactivation of latent HIV infection from thymocytes and peripheral blood lymphocytes (PBLs) in the severe combined immunodeficient mouse containing human fetal thymus and liver cells (SCID-hu [Thy/Liv] mouse; Brooks et al., 2001, *Nat Med* 7:459-464; Korin et al., 2002, *J Virol* 76(16):8118-23).

In addition, the small molecules described herein and agents derived therefrom through routine chemical manipulations that are useful for purging a latent HIV reservoir can be tested for their potential to activate latent HIV expression by real time PCR detecting viral transcripts as described herein and as known in the art.

HDAC inhibitors described herein and agents derived therefrom through routine chemical manipulations that are useful for purging a latent HIV reservoir can be tested in chromatin immunoprecipitation assays measuring their capability to deacetylate the HIV promoter as described (Ylisastigui et al., 2004, *AIDS* 18(8):1101-8; Williams et al., 2004, *J Biol Chem* 279(40):42008-42017). The effect of HDAC inhibitors on resting $CD4^+$ T cell phenotype can be measured by flow cytometric analysis (Ylisastigui et al., 2004, *AIDS* 18(8):1101-8).

Other HDAC inhibitors and agents derived therefrom through routine chemical manipulations may also be tested in the presence and absence of a candidate substance, such as a histone with a labeled acetyl group. For example, a method generally comprises: (a) providing a candidate HDAC inhibitor, (b) combining the candidate HDAC inhibitor with an HDAC; (c) measuring HDAC activity, and (d) comparing the activity in step (c) with the activity in the absence of the candidate HDAC inhibitor, wherein a lower measured activity in (b) when compared to the measured activity without the candidate HDAC inhibitor indicates that the candidate HDAC inhibitor is, indeed an HDAC inhibitor.

III. Synergistic Effect of Inhibitors of Histone Deacetylase and Activators of Latent HIV Expression The compounds of the present invention, inhibitors of HDAC and activators of latent HIV expression find use in a variety of ways. The present invention discloses the surprising finding that HDAC inhibitors, such as TSA and valproic acid, which typically have no substantial effect on the expression of latent HIV expression, can potentiate the expression of latent HIV-1 above an expression level obtained by administration of an activator of latent HIV expression, such as prostratin, alone. That is, inhibitors of HDAC synergize with activators of latent HIV expression. Because inhibitors of histone deacetylase synergize with an activator of latent HIV expression, and in particular prostratin, a lower dose of the activator of latent HIV expression can be used to essentially obtain the same or greater effect on activation of latent HIV expression than would be obtained when using the activator of latent HIV expression alone. Thus, using a much lower dose of, for example, prostratin, potentially avoids its toxicity at full dose.

Methods of the present invention can be practiced in vitro and in vivo. In a preferred embodiment, the step of administering a composition according to the present invention is performed in vivo, for example, by an intradermal, intravenous, subcutaneous, oral, aerosol, intramuscular and intraperitoneal route of administration, or ex vivo, for example, by transfection, electroporation, microinjection, lipofection, adsorption, protoplast fusion, use of protein carrying agents, use of ion carrying agents, and use of detergents for cell permeabilization.

A. Method for Activating Latent HIV Expression

In a preferred embodiment the present invention provides a method for activating latent HIV expression in a mammalian cell having an integrated HIV genome, the method comprising the steps of (a) contacting the mammalian cell with an amount of an activator of latent HIV expression effective to activate latent HIV expression to a first expression level; and (b) contacting the mammalian cell with an amount of an inhibitor of histone deacetylase effective to activate the latent HIV expression to a second expression level, wherein the activator of latent HIV expression and the inhibitor of histone deacetylase synergize to generate the second expression level.

In a preferred embodiment of the present invention, the activator of latent HIV expression and the inhibitor of histone deacetylase are used simultaneously for the contacting of the mammalian cell. This can be done by contacting the mammalian cell with a composition comprising both compounds as further described herein. In other embodiments, the activator of latent HIV expression and the inhibitor of histone deacetylase are used sequentially.

In another preferred embodiment the present invention provides a method for activating latent HIV expression in a mammalian cell having an integrated HIV genome, the method comprising the steps of (a) contacting the mammalian cell with an amount of an activator of latent HIV expression effective to activate latent HIV expression; and (b) contacting the mammalian cell with an amount of an inhibitor of histone deacetylase effective to further activate the latent HIV expression, wherein the activation of latent HIV expression after step (b) is greater than the activation of latent HIV expression by step (a) alone; wherein the level of the HIV RNA in the mammalian cell is increased.

The HIV genome is integrated in the genome of the mammalian cell.

It is understood, that this method results in an increase of the activity of an LTR promoter in the mammalian cell leading to a more processive RNA polymerase II complex.

In a preferred embodiment, this method comprises the step of contacting a mammalian cell with an amount of Tat effective to activate latent HIV expression above the level exhibited by steps (a) and (b); wherein the level of the HIV RNA in the mammalian cell is further increased.

In another preferred embodiment, this method comprises the step of contacting a mammalian cell with an amount of NF-κB effective to activate the latent HIV expression above the level exhibited by steps (a) and (b); wherein the level of the HIV RNA in the mammalian cell is further increased.

In a preferred embodiment, the step of contacting a compound or composition of the invention with a mammalian cell is performed by administering the compound or composition to a mammalian cell in a human, preferably a human having a latent HIV infection.

The methods of the present invention can be applied to any cell wherein an HIV genome is integrated into the cellular DNA, preferably a mammalian cell and even more preferred a human cell. A preferred cell is a resting lymphoid mononuclear cell obtained from a mammal including e.g., lymphocytes, such as T cells (CD4, CD8, cytolytic, helper), B cells, natural killer cells; mononuclear phagocytes, such as monocytes, macrophages, epitheloid cells, giant cells, microglia, Kupffer cells, alveolar macrophages; dendritic cells, such as interdigitating dendrite cells, Langerhans cells, or follicular dendritic cells; granulocytes; etc. Preferred is a $CD4^+$ T cell.

In another preferred embodiment, a preferred cell is a myeloid mononuclear cell, preferably, a peripheral blood mononuclear cell or tissue macrophage.

Another surprising finding of this invention is that because of inhibitors of histone deacetylase synergize the effect, an activator of latent HIV expression, and in particular prostratin, has on the activation of latent HIV expression, a lower dose of the activator of latent HIV expression can be used to essentially obtain the same or greater effect on activation of latent HIV expression than would be obtained when using the activator of latent HIV expression alone. Thus in a preferred embodiment, the amount of an activator of latent HIV expression, e.g., prostratin, contacting the mammalian cell is less than 50% of an amount of an activator of latent HIV expression, e.g., prostratin, that is required to obtain the same second expression level in the absence of trichostatin A. In another embodiment the amount of an activator of latent HIV expression, e.g., prostratin, contacting the mammalian cell is less than 25%, preferably less than 20%, preferably less than 10%, more preferably less than 5% and even more preferably less than 2% of an amount an activator of latent HIV expression, e.g., prostratin, that is required to obtain the same second expression level in the absence of trichostatin A.

B. Method for Treating HIV Latency

In a preferred embodiment of the present invention the composition of the invention are used in a method for treating HIV latency. This method can be practiced in vitro. Preferably this method is practiced in vivo. Preferably this method is practiced in a host latently infected with HIV, e.g., a human latently infected with HIV. This method seeks to complete eradicate a latent HIV reservoir in a latently HIV infected subject.

This method comprises the steps of administering to the latently HIV-infected host a therapeutically effective amount of a composition comprising an activator of latent HIV expression and an HDAC inhibitor.

When practiced in vivo, the method, optionally comprises the step of administering HAART. Thus, in yet another embodiment of the present invention, a method of treating a latently HIV-infected host comprises the step of administering highly active antiretroviral therapy (HAART).

According to this embodiment, a composition comprising an activator of latent HIV expression and an HDAC inhibitor may be coadministered with any HAART regimen. The current standard of care using HAART is usually a combination of at least three nucleoside reverse transcriptase inhibitors and frequently includes a protease inhibitors, or alternatively a non-nucleoside reverse transcriptase inhibitor. Patients who have low $CD4^+$ cell counts or high plasma RNA levels may require more aggressive HAART. For patients with relatively normal $CD4^+$ cell counts and low to non-measurable levels of plasma HIV RNA over prolonged periods (i.e. slow or non-progressors) may require less aggressive HAART. For anti-retroviral-naive patients who are treated with initial antiretroviral regimen, different combinations (or cocktails) of antiretroviral drugs can be used.

Preferably, a composition comprising an activator of latent HIV expression and an HDAC inhibitor may be coadministered with a "cocktail" of nucleoside reverse transcriptase inhibitors, non-nucleoside HIV reverse transcriptase inhibitors, and protease inhibitors. For example, a composition comprising an activator of latent HIV expression and an HDAC inhibitor may be coadministered with a cocktail of two nucleoside reverse transcriptase inhibitors (e.g. ZIDOVUDINE (AZT) and LAMIVUDINE (3TC)), and one protease inhibitor (e.g. INDINAVIR (MK-639)). A composition comprising an activator of latent HIV expression and an HDAC inhibitor may also be coadministered with a cocktail of one nucleoside reverse transcriptase inhibitor (e.g. STAVUDINE (d4T)), one non-nucleoside reverse transcriptase inhibitor (e.g. NEVIRAPINE (BI-RG-587)), and one protease inhibitor (e.g. NELFINAVIR (AG-1343)). Alternatively, a composition comprising an activator of latent HIV expression and an HDAC inhibitor may be coadministered with a cocktail of one nucleoside reverse transcriptase inhibitor (e.g. ZIDOVUDINE (AZT)), and two protease inhibitors (e.g. NELFINAVIR (AG-1343) and SAQINAVIR (Ro-31-8959)).

Coadministration in the context of this invention is defined to mean the administration of more than one therapeutic in the course of a coordinated treatment to achieve an improved clinical outcome. Such coadministration may also be coextensive, that is, occurring during overlapping periods of time. Further discussion of such conventional treatment can be found in the art (e.g., Gulick, 1997; *Qual Life Res* 6:471-474; Henry et al., 1997, *Postgrad Med* 102:100-107; Hicks, 1997, *Radiol Clin North Am* 35:995-1005; Goldschmidt, 1996, *Am Fam Physician* 54:574-580).

This regimen is continued for a period past the point when the levels of integrated and unintegrated HIV in active and memory T cells are undetectably low. At the end of the period, the patient is weaned from HAART and from the activators of latent HIV expression and HDAC inhibitors according to the invention. At this point, the patient is monitored for reestablishment of normal immune function and for signs of reemergence of HIV infection. Additionally, any needed conjunctive immunotherapy, such as bone marrow transplants, various cytokines or vaccination, may be administered. After this, the patient is monitored on a routine basis for life to detect reemergence of HIV infection, in which case repeat therapy according to the above preferred embodiment is recommended.

C. Method for Rendering Latent HIV Sensitive to Killing by an Immunotoxin

Several immunotoxins can be employed in this method. A preferred immunotoxin is an immunotoxin targeted to an HIV protein expressed on the exterior of cells, such as the viral envelope glycoprotein or a portion thereof. The term "immunotoxin" refers to a covalent or non-covalent linkage of a toxin to an antibody, such as an anti HIV envelope glycoprotein antibody. The toxin may be linked directly to the antibody, or indirectly through, for example, a linker molecule. A preferred toxin is a toxin selected from the group consisting of ricin-A and abrin-A.

D. General Method

Activation of latent HIV expression (also referred to as reactivation of latent HIV expression) results in the conversion of latently infected cells to productively infected cells. This transition can be measured by any characteristic of active viral infection, e.g., production of infectious particles, reverse transcriptase activity, secreted antigens, cell-surface antigens, soluble antigens, HIV RNA and HIV DNA, etc.

The methods of the present invention described above, may optionally comprise the step of determining or detecting activation of latent HIV expression. In one embodiment, such a method comprises determining or detecting a mRNA, preferably an HIV mRNA. Other mRNAs, such as Tat mRNA, NF-κB mRNA, NF-AT mRNA and other mRNAs encoding polypeptides described herein can also be determined using the following methods.

1. Detection of mRNA

A preferred mRNA is an HIV mRNA. Thus, expression levels of HIV mRNA, may be determined. Detecting a increased expression level of the HIV mRNA relative to the mRNA level present in a latently infected cell indicates activation of the latent HIV expression. In one embodiment, the step of determining the level of the HIV mRNA comprises an amplification reaction. Methods of evaluating mRNA expression of a particular gene are well known to those of skill in the art, and include, inter alia, hybridization and amplification based assays.

a) Direct Hybridization-Based Assays

Methods of detecting and/or quantifying the level of a gene transcript (mRNA or cDNA made therefrom) using nucleic acid hybridization techniques are known to those of skill in the art. For example, one method for evaluating the presence, absence, or quantity of HIV polynucleotides involves a Northern blot. Gene expression levels can also be analyzed by techniques known in the art, e.g., dot blotting, in situ hybridization, RNase protection, probing DNA microchip arrays, and the like (e.g., see Sambrook, J., Fritsch, E. F., and Maniatis, "Molecular Cloning A Laboratory Manual" by T. published by Cold Spring Harbor Laboratory Press, 2nd edition, 1989).

b) Amplification-Based Assays

In another embodiment, amplification-based assays are used to measure the expression level of an HIV gene. In such an assay, the HIV nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of HIV mRNA in the sample. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). Exemplary methods using HIV nucleic acids as a template for PCR are described as well (E.g., see (Williams et al., 2004, *J Biol Chem* 279(40):42008-42017; Williams et al., 2006, *EMBO J* 25:139-149).

In one embodiment, a TaqMan based assay is used to quantify the HIV polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, Heid et al., 1996, *Genome Res* 6(10):986-94; Morris et al., 1996, *J Clin Microbiol* 34(12):2933-6).

Other suitable amplification methods include, but are not limited to, ligase chain reaction (LCR) (see, Wu and Wallace, 1989, *Genomics* 4:560; Landegren et al., 1988, *Science* 241: 1077; and Barringer et al., 1990, *Gene* 89:117), transcription amplification (Kwoh et al., 1989, *Proc Natl Acad Sci USA* 86:1173), self-sustained sequence replication (Guatelli et al., 1990, *Proc Nat Acad Sci USA* 87: 1874), dot PCR, and linker adapter PCR, etc.

2. Detection of Polypeptide

The methods of the present invention described above, may optionally comprise the step of determining or detecting activation of latent HIV expression. In one embodiment, such a method comprises determining or detecting a polypeptide, preferably an HIV polypeptide or a polypeptide for which the coding region has been inserted into the HIV genome, such as the GFP polypeptide of the J-Lat cell lines described herein and by Jordan et al., (Jordan et al., 2003, *EMBO J* 22(8):1868-1877). Other polypeptides, such as Tat, NF-κB, NF-AT and others described herein can also be determined using the following methods.

Thus, expression level of an HIV polypeptide may be determined by several methods, including, but not limited to, affinity capture, mass spectrometry, traditional immunoassays directed to HIV proteins (such as gp120 and reverse transcriptase), PAGE, Western Blotting, or HPLC as further described herein or as known by one of skill in the art.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

3. Determining Latent Viral Load

Methods and compositions for determining latent viral load have been described, e.g., in U.S. Pat. Appl. Publ. 2001/0039007, published Nov. 8, 2001, incorporated herewith by reference in its entirety.

IV. Pharmaceutical Compositions

In one aspect the present invention provides a pharmaceutical composition or a medicament comprising at least an activator of latent HIV expression and an inhibitor of HDAC of the present invention and optionally a pharmaceutically acceptable carrier. A pharmaceutical composition or medicament can be administered to a subject for the treatment of, for example, a condition or disease as described herein.

A pharmaceutical composition may include any combinations of latent HIV activator compounds, HIV transcription activators and HDAC inhibitors.

A. Formulation and Administration

Compounds of the present invention, such as the activators of latent HIV expression and the inhibitors of HDAC described herein, are useful in the manufacture of a pharmaceutical composition or a medicament comprising an effective amount thereof in conjunction or mixture with excipients or carriers suitable for either enteral or parenteral application.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. The small molecule compounds of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In one embodiment of the present invention, a pharmaceutical composition or medicament comprises an effective amount of an activator of latent HIV expression and an inhibitor of HDAC of the present invention as defined above, and another therapeutic agent, such as a component used for HAART, as described herein. When used with compounds of the invention, such therapeutic agent may be used individually (e.g., a component used for HAART and compounds of the present invention), sequentially (e.g., a component used for HAART and compounds of the present invention for a period of time followed by e.g., a second component used for HAART and compounds of the present invention), or in combination with one or more other such therapeutic agents (e.g., a reverse transcriptase inhibitor used for HAART, a protease inhibitor used for HAART, and compounds of the present invention). Administration may be by the same or different route of administration or together in the same pharmaceutical formulation.

Thus, in a preferred embodiment of the present invention, a pharmaceutical composition comprises (i) an activator of latent HIV expression, (ii) an inhibitor of histone deacetylase, and (iii) a pharmaceutically acceptable carrier.

In another preferred embodiment of the present invention, a pharmaceutical composition comprises (i) an activator of NF-κB or NF-AT, (ii) an inhibitor of histone deacetylase, and (iii) a pharmaceutically acceptable carrier.

B. Therapeutic Effective Amount and Dosing

In one embodiment of the present invention, a pharmaceutical composition or medicament is administered to a subject, preferably a human, at a therapeutically effective dose to prevent, treat, or control a condition or disease as described herein, such as HIV latency. The pharmaceutical composition or medicament is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose."

The dosage of active compounds administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In one embodiment of the present invention, a pharmaceutical composition or medicament comprising compounds of the present invention is administered in a daily dose in the range from about 0.1 mg of each compound per kg of subject weight (0.1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, activators of latent HIV expression and inhibitors of HDAC may be administered in different amounts and at different times.

The recommended initial dose for VpA, in the treatment of seizures (see above), for example, is 15 mg/kg/day orally, increasing at 1-week intervals by 5-10 mg/kg/day until seizures are controlled or side effects preclude further increases. A maximum recommended dose is 60 mg/kg/day. When the total daily dose exceeds 250 mg, it should be given in a divided regimen. A similar dosing regimen may be used for VpA in the methods of the present invention.

To achieve the desired therapeutic effect, compounds may be administered for multiple days at the therapeutically effective daily dose. Thus, therapeutically effective administration of compounds to treat a condition or disease described herein in a subject requires periodic (e.g., daily) administration that continues for a period ranging from three days to two weeks or longer. Typically, compounds will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the compounds every other day, every third day, or, if higher dose ranges are employed and tolerated by the subject, once a week. A preferred dosing schedule, for example, is administering daily for a week, one week off and repeating this cycle dosing schedule for 3-4 cycles.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Following successful treatment, it may be desirable to have the subject undergo maintenance therapy to prevent the recurrence of the condition or disease treated.

V. Kits

For use in diagnostic, research, and therapeutic applications suggested above, kits are also provided by the invention. In the diagnostic and research applications such kits may include any or all of the following: assay reagents, buffers, a compounds of the present invention, an HIV polypeptide, an HIV nucleic acid, an anti-HIV polypeptide antibody, hybridization probes and/or primers, expression constructs for e.g., Tat, NF-κB, or NF-AT, etc. A therapeutic product may include sterile saline or another pharmaceutically acceptable emulsion and suspension base.

In a preferred embodiment of the present invention, a kit comprises one or more activators of latent HIV expression and one or more inhibitor of HDAC. Optionally, the kit includes one or more components used for HAART as described herein. Typically, these compounds are provided in a container.

This invention provides kits for eliminating a latent HIV reservoir in a mammalian cell. In a preferred embodiment of the present invention this kit comprises (i) a first container containing an activator of latent HIV expression, (ii) a second container containing an inhibitor of histone deacetylase, and (iii) an instruction for using the activator of latent HIV expression and the inhibitor of histone deacetylase for eliminating the latent HIV reservoir in the mammalian cell.

In another preferred embodiment of the present invention this kit comprises (i) a first container containing an inducer of NF-κB or NF-AT, (ii) a second container containing an inhibitor of histone deacetylase, and (iii) an instruction for using the inducer of NF-κB or NF-AT and the inhibitor of histone deacetylase for eliminating the latent HIV reservoir in the mammalian cell.

In addition, a kit may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In a preferred embodiment of the present invention, the kit comprises an instruction for using an activator of latent HIV expression and an inhibitor of HDAC for increasing the level of latent HIV expression above the level of latent HIV expression induced by the activator of latent HIV expression alone.

Optionally, the instruction comprises warnings of possible side effects and drug-drug or drug-food interactions.

A wide variety of kits and components can be prepared according to the present invention, depending upon the intended user of the kit and the particular needs of the user.

In a preferred embodiment of the present invention, the kit is a pharmaceutical kit and comprises a pharmaceutical composition comprising (i) an activator of latent HIV expression, (ii), an inhibitor of HDAC, and (iii) a pharmaceutical acceptable carrier. Optionally, the pharmaceutical kit comprises a Tat. In another preferred embodiment, the pharmaceutical kit comprises a component for use in HAART as described herein. Pharmaceutical kits optionally comprise an instruction stating that the pharmaceutical composition can or should be used for treating a condition or disease described herein.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

EXAMPLES

Example 1

General Methods

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed., 1984), *Animal Cell Culture* (R. I. Freshney, Ed., 1987), the series *Methods In Enzymology* (Academic Press, Inc.); *Gene Transfer Vectors For Mammalian Cells* (J. M. Miller and M. P. Calos eds. 1987), *Current Protocols In Molecular Biology* (F. M. Ausubel, R. Brent, R. E. Kingston, D. D. Moore, J. G. Siedman, J. A. Smith, and K. Struhl, eds., 1987).

A. Cell Culture

J-Lat 6.3, J-Lat 8.4 T-cells, and J-Lat 9.2 cells are Jurkat T cell lines containing integrated but transcriptionally latent HIV proviruses. These J-Lat cells contain wild-type Tat and TAR and appear to be highly representative of the latently infected cells present in vivo (Williams et al., 2004, *J Biol Chem* 279(40):42008-42017).

J-Lat 6.3 T cells, J-Lat 8.4 T-cells and J-Lat 9.2 T cells were obtained from Jordan et al., (Jordan et al., 2003, *EMBO J* 22(8):1868-1877). J-Lat cells were cultured in RPMI supplemented with 10% fetal calf serum (FCS) and penicillin/streptomycin and L-glutamine described (Williams et al., 2004, *J Biol Chem* 279(40):42008-42017; Williams et al., 2006, *EMBO J* 25:139-149).

Typically, cells were stimulated with prostratin (LC Laboratories), from about 0.1 to about 10 μM; with TNF-α (R&D Systems) at 10 ng/ml; with 4-α-phorbol 12-myristate 13-acetate (PMA); with trichostatin A (TSA) at concentration s ranging from about 50-400 nM, with valproic acid (Sigma) at concentrations ranging from 0.3-3 mM; or combinations of one or more of these compounds (see the following Examples for details).

B. Cell Viability Assay

Following stimulation, cells were cultured for 16 hours at 37° C. 90% humidity, 5% CO2. Cells were then analyzed by flow cytometry for viability.

Cells were scored as viable if they were detected in a characteristically "live" region of light scatter and defraction as measured by flow cytometry.

C. Cell Transfection Assays

Cell transfection assays were essentially performed as described (Williams et al., 2004, *J Biol Chem* 279(40):42008-42017; Williams et al., 2006, *EMBO J* 25:139-149).

$10^6$ J-Lat 6.3 cells cultured in RPMI+10% fetal calf serum (FCS) and penicillin/streptomycin were pelleted by centrifugation and resuspended in 0.4 mL RPMI without serum. Cell suspension was mixed with 1 µg of pMACS-kk H2kk expression vector DNA (Miltenyi), and 10 µg of pCMV4 (Andersson et al., 1989, *J Biol Chem* 264 (14):8222-8229), or 10 µg pCMV4-FLAG-Tat expression vector (gift of Eric Verdin), transferred to a 0.4 cm gap electroporation cuvette (Stratagene), and electroporated at 975 µF, 250 mV for ~25×10⁻³ seconds. Electroporated cells were resuspended in 4 mL medium, and returned to cell culture for 48 hours. 90 µl aliquots of each sample were distributed to U-bottomed 96-well plates and 10 µl of 200 ng/mL TNF-α (Biosource), 10 µl of 1 mM Trichostatin A (Biomol), or 10 µl of RPMI. For 30'-pulse TNF-α stimulation experiments, 10 µl of 200 ng/mL TNF-α was added to 90 µl cell suspension for 30 minutes, cells were transferred to a V-bottomed 96 well plate and centrifuged at 1800 RPMI for 3 minutes. Supernatant was removed and replaced, and procedure was repeated 2×. Cells were resuspended in 100 µl fresh RPMI with 10% serum and penicillin/streptomycin. 16 hours after treatment, cells were pelleted by centrifugation, and resuspended in 50 µl PBS+1:100 dilution of streptavidin-conjugated anti-H2kk antibody. Samples were incubated 10 minutes, diluted in 200 µl PBS, pelleted by centrifugation, and supernatant removed. Cells were resuspended in 50 µl PBS+1:100 dilution of biotin-allophycoerythrin (APC), incubated 10 minutes, diluted in 200 µl PBS, pelleted by centrifugation, supernatant removed, resuspended in 100 µl PBS, pelleted by centrifugation, supernatant removed and resuspended in 50 µl PBS. Samples were analyzed by flow cytometry using a Beckton Dickinson FACSCalibur. Cells were analyzed using FlowJo (TreeSoft) flow cytometry analysis software. Live cells were identified by characteristic light scatter and defraction and exclusively analyzed. Cells with APC fluorescence greater that untransfected cells stained with biotin-APC were considered to be H2kk-positive, and to have been successfully transfected. Subsequent analyses were restricted to this subset of cells D. HIV Immunoassays (Western Blotting)

Immunoblotting analysis can essentially be performed as described (Williams et al., 2004, *J Biol Chem* 279(40):42008-42017).

J-Lat 6.3 or 9.2 cells were adjusted to 1×10⁶ cells/ml and stimulated with TNF-α or prostratin for various times. Cells were then lysed on ice in egg lysis buffer (50 mM HEPES, pH 7, 250 mM NaCl, 1% Nonidet P-40, 5 mM EDTA) for 20 mM and clarified by microcentrifugation. Lysates were next added to an equal volume of 2× Laemmli buffer (25 mM Tris, 200 mM glycine, 0.1% SDS) and heated to 95° C. for 5 min. Proteins were separated by SDS-PAGE, transferred to polyvinylidene difluoride membranes, and immunoblotted with various antibodies.

E. HIV-LTR-Driven Expression of GFP

The J-Lat T-cell clones used herein are infected with full-length HIV proviruses and contain the *Aequorea victoria* green fluorescent protein (GFP) gene in lieu of Net thus permitting epifluorescence monitoring of viral transcriptional activity. Under basal conditions, little or no GFP expression is detected; however, transcriptional activation of the latent provirus leads to GFP expression, which can be detected at the single-cell level by flow cytometry. Flow cytometry analysis and FACS was essentially performed as described (Williams et al., 2004, *J Biol Chem* 279(40):42008-42017).

Cells were analyzed for GFP-fluorescence and general viability characteristics on a FACSCalibur flow cytometer (Becton Dickinson). Data were analyzed with FlowJo (Treesoft) flow cytometry analysis software.

F. Detection of HIV mRNA

1. RNA Analysis

RNA extraction and analysis of initiated and elongated HIV transcripts can be performed as described (Williams et al., 2006, *EMBO J* 25:139-149)

2. Semi-Quantitative PCR

PCR analysis can essentially be performed as described (Williams et al., 2004, *J Biol Chem* 279(40):42008-42017; Williams et al., 2006, *EMBO J* 25:139-149).

J-Lat 6.3 cells (1×10⁶ cells/mi) were treated with TSA (100 nM) or TNF-α(20 ng/ml) for 2 h at 37° C. For analysis of HIV mRNA synthesis in nucleofected primary T cells, RNA was extracted from 0.5×10⁶ cells with an RNA Wiz kit (Ambion). RNA transcripts were quantitated with the QuantiTect SYBR Green RT-PCR kit (Qiagen). To quantitate viral transcripts, serial dilutions of a quantitated RNA stock of full-length viral genome were used as a reference standard (gift of R Grant). Initiated transcripts were detected with primers HIVTAR5 (5'-GTTAGACCAGATCTGAGCCT-3') [SEQ ID NO: 1] and HIVTAR3 (5'-GTGGGTTCCCTAGTTAGCCA-3') [SEQ ID NO: 2]. Elongated transcripts were detected with primers HIVTat5 (5'-ACTCGACAGAGGAGAGCAAG-3') [SEQ ID NO: 3] and HIVtat3 (5'-GAGTCTGACTGTTCTGATGA-3') [SEQ ID NO: 4]. β-Actin mRNA copies were quantitated with primers β-actin5 (5'-GTCGACAACGGCTCCGGC-3') [SEQ ID NO: 5] and β-actin3 (5'-GGTGTGGTGCCA-GATTTTCT-3') [SEQ ID NO: 6] specific for a 239 bp region in the β-actin mRNA and samples were normalized for β-actin copies. Fluorescence profiles were collected on an ABI 7700 real-time thermal cycler and analyzed with SDS v1.91 (Applied Biosystems). The absence of nonspecific bands in RT-PCR products was confirmed on 2% agarose gels.

Example 2

TSA Synergizes with Prostratin to Activate Latent HIV Expression

Figure 1B:
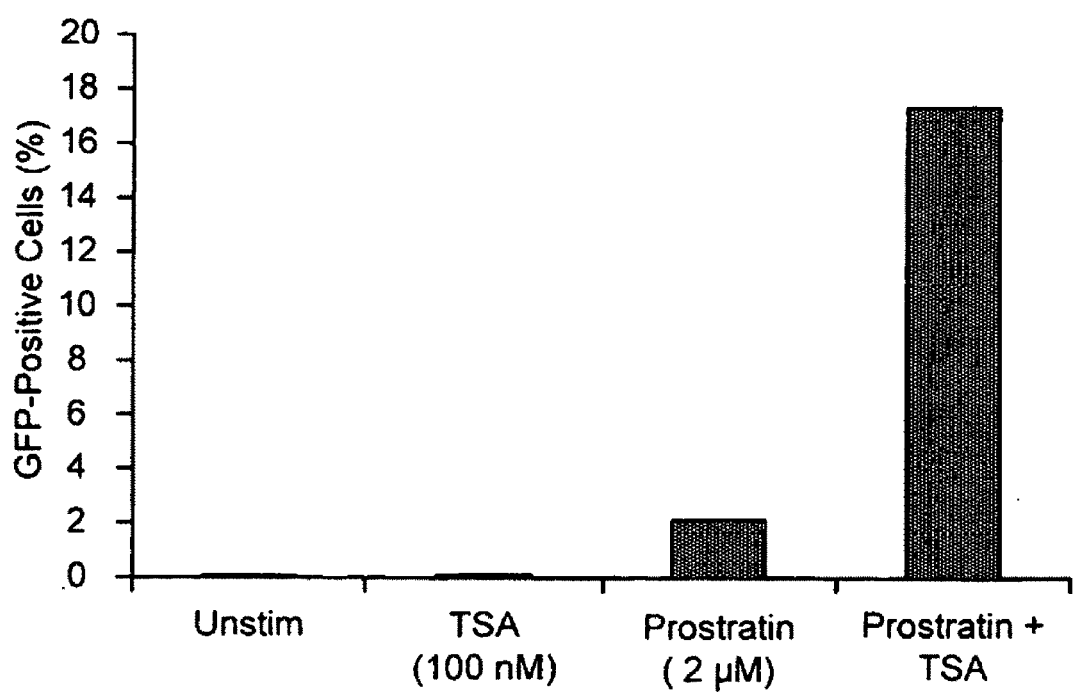

J-Lat 6.3 and 8.4 T-cells cultured in RPMI supplemented with 10% fetal calf serum (FCS) and penicillin/streptomycin were counted and adjusted to 1×10⁶ cells/ml. 80 µl aliquots of J-Lat 6.3 and 8.4 T-cells, respectively, were pipetted in a 96-well u-bottomed plate. 10 µl of 20 µM prostratin (final concentration 2 µM; LC Laboratories) were added to prostratin stimulated cell samples. 10 µl cell culture medium were added to unstimulated cells. 10 µl of 1 µM trichostatin A (final concentration of 100 nM; BIOMOL) were added to TSA-stimulated cell samples. 10 µl cell culture medium were added to unstimulated cells. One cell sample of J-Lat 6.3 and 8.4 T-cells was incubated with prostratin (2 µM) and TSA (100 nM). Samples were mixed by pipetting, returned to a 37° C. incubator with 5% $CO_2$ and 90% humidity for 16 hours. Then HIV-LTR-driven expression of GFP was assessed by flow cytometry using a Beckton Dickenson FACScalibur as described above. Data analysis was performed using Treesoft FlowJo software. Cells with greater GFP fluorescence than a non-GFP expressing Jurkat control cells were considered GFP-positive. These experiments showed that prostratin induced the activation of latent HIV expression. Although TSA had no significant effect when administered alone, it potentiated the effect of prostratin about 5-6 fold in J-Lat 6.3 cells (FIG. 1A) and about 6-7 fold in 8.4 T-cells (FIG. 1B). This experiment showed that TSA synergizes with prostratin to activate latent HIV expression.

Figure 1C:
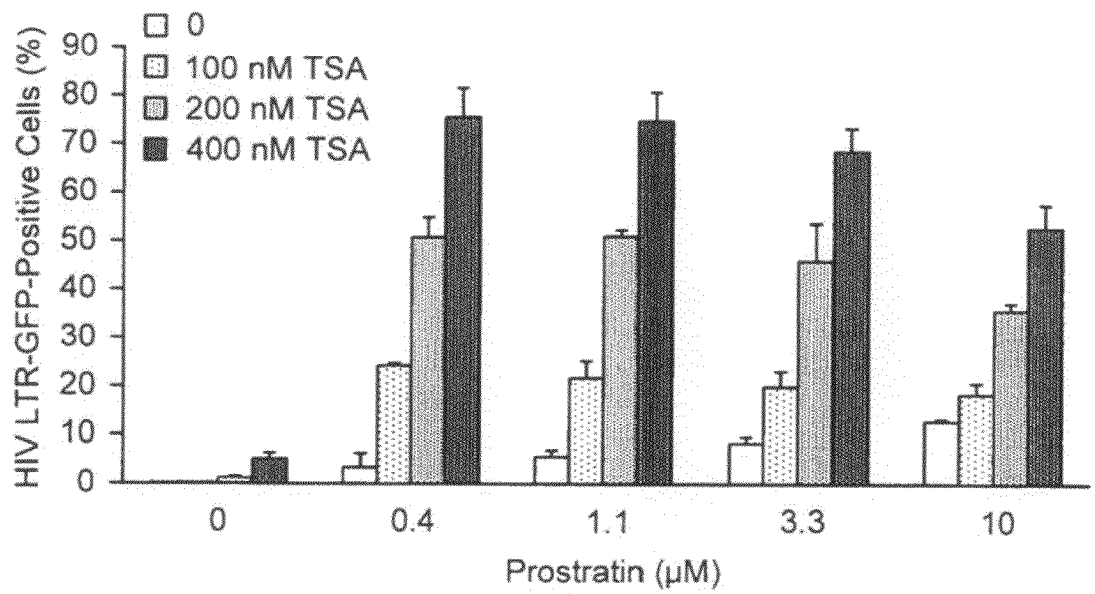

In a similar experiment, J-Lat6.3kRed2 cells, a modified cell line derived from J-Lat6.3 containing an integrated kB-DsRed2 reporter, was used. J-Lat6.3kRed2 cells were counted and adjusted to $1 \times 10^6$ cells/ml. 80 µl aliquots were pipetted in a 96-well u-bottomed plate. Two-fold serial dilutions of 4, 2, and 1 µM trichostatin A (TSA) were made and added to the cells at final concentrations of 400 nM, 200 nM, and 100 nM, respectively. Three-fold serial dilutions of 100, 33, 11, 3.7 µM prostratin were made and added to cells at final concentrations of 10 µM, 3.3 µM, 1.1 µM, and 0.37 µM (0.4 µM in FIG. 1C), respectively. Samples were mixed by pipetting, returned to a 37° C. incubator with 5% $CO_2$ and 90% humidity for 20 hours, HIV-LTR-driven expression of GFP was assessed by flow cytometry as described above. This experiment showed that TSA had a drastic effect on the activation of latent HIV expression. The synergistic effect observed with 370 (400) nM TSA, for example, was about 16 fold when used in combination with 0.4 µM prostratin. A representative result of this experiment is shown in FIG. 1C.

Example 3

Administration of TSA Reduces Prostratin-Induced Cell Death

Figure 2A:
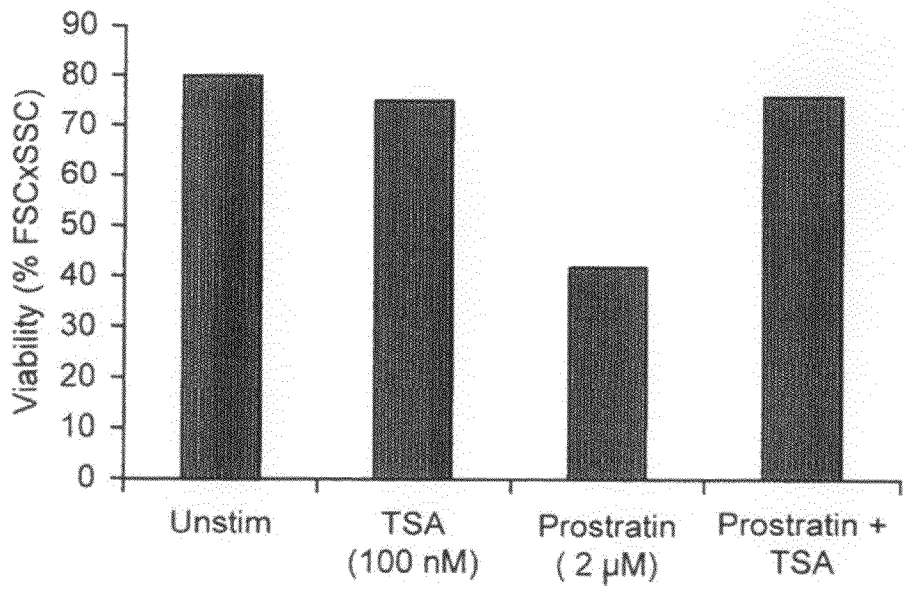
FIG. 2 shows that administration of TSA reduces prostratin-induced cell death. A. Administration of TSA reduces prostratin-induced cell death in J-Lat 6.3 cells. B. Administration of TSA reduces prostratin-induced cell death in J-Lat 8.4 cells. In A. and B., TSA was used at a concentration of 100 nM and prostratin at a concentration of 2 µM, respectively. C. Administration of TSA reduces prostratin-induced cell death in J-Lat 6.3 cells over a wide range of prostratin concentrations. TSA and prostratin were used at the concentrations indicated. Cell viability is indicated as % FsC×SSC. Unstim, unstimulated. Details are described in Example 3.
Figure 2B:
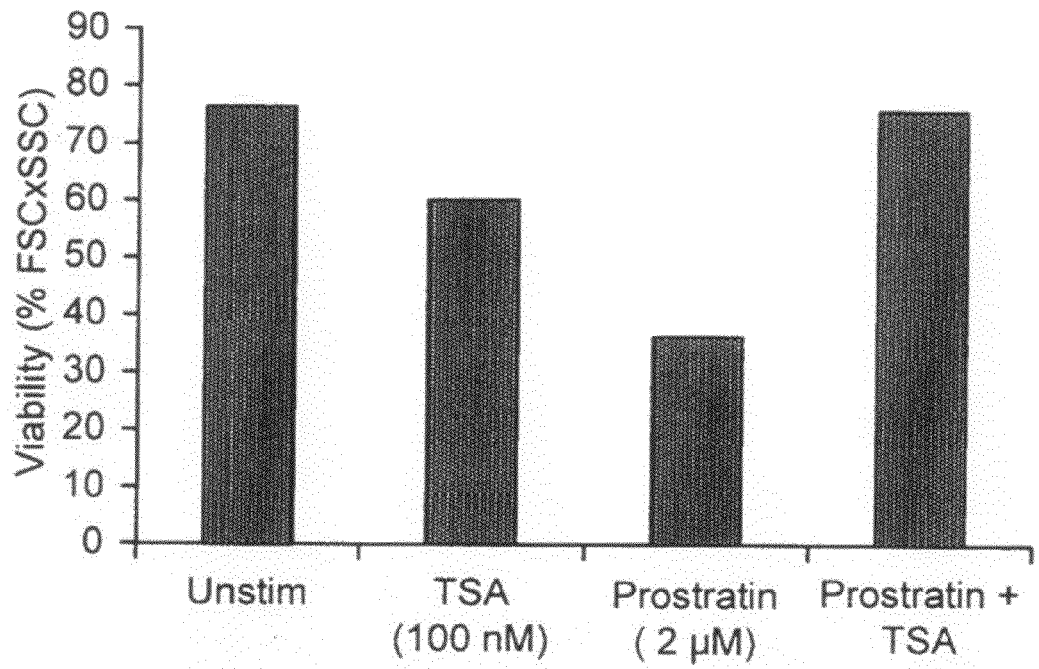
Figure 2C:
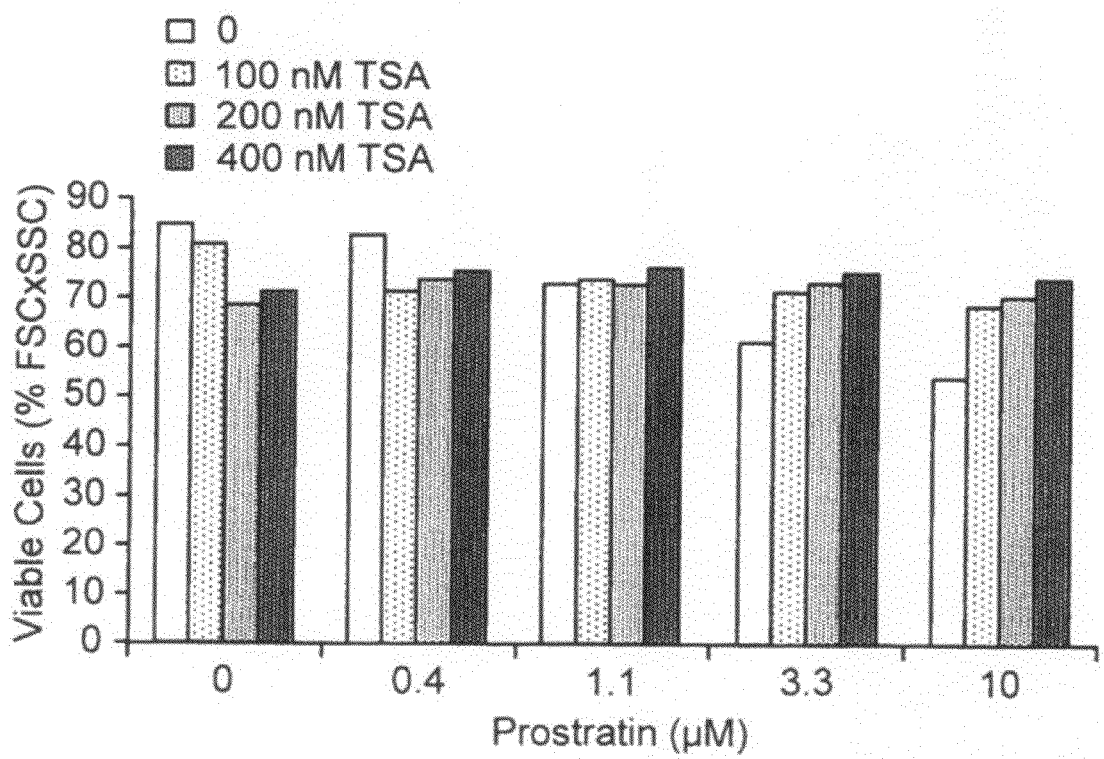

As described herein, it is known in the art that high concentrations of prostratin exert some toxic effects on cells. Thus, using the same experimental set-up as described in Example 2, above, cell viability was determined. Cell viability were quantitated as described above. Using J-Lat 6.3 cells and 8.4 T-cells, it was observed that 2 µM prostratin induced cell death in about 50% of the cells. Upon co-administration of 100 nM TSA, the prostratin-induced cell death was almost completely inhibited. A representative result is shown in FIGS. 2A and 2B. A similar effect was observed in J-Lat6.3kRed2 cells (using the set-up as described in Example 2). TSA inhibited prostratin-induced cell death even when prostratin was used at a concentration of 10 µM (FIG. 2C). In this experiment, cells were incubated with prostratin for about 20 hours, whereas J-Lat 6.3 cells and 8.4 T-cells (in FIGS. 2A and 2B) were incubated with prostratin for 36 hours. Thus, a higher cell death was observed with longer prostratin treatment.

Example 4

Valproic Acid Synergizes with Prostratin to Activate Latent HIV Expression

Figure 3:
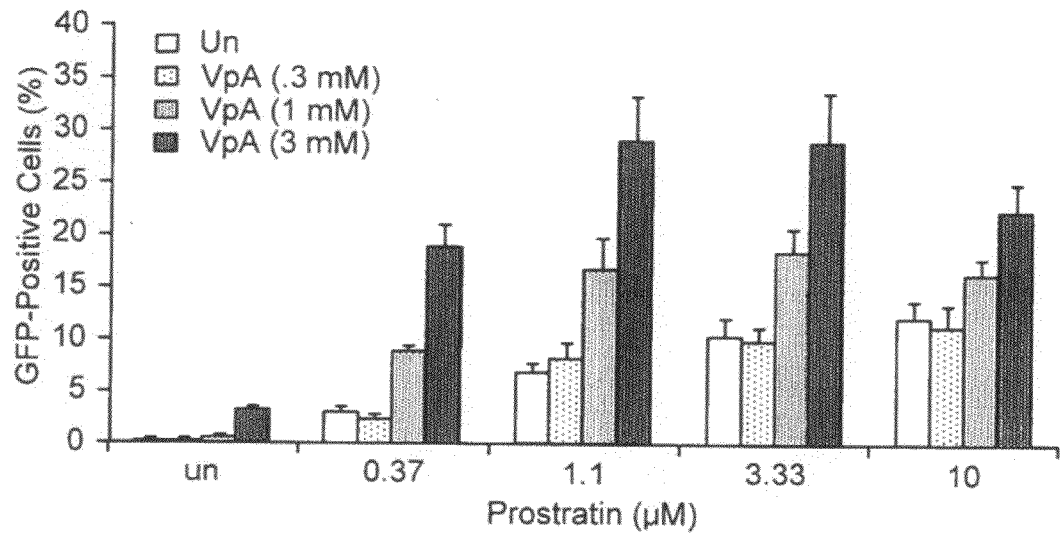
FIG. 3 shows that valproic acid (VpA) synergizes with prostratin to activate latent HIV expression in J-Lat 6.3 cells. HIV expression was determined as % of GFP-positive cells. VpA and prostratin were used at the concentrations indicated. un, unstimulated. Details are described in Example 4.

In order to test a possible synergistic effect of additional histone deacetylase inhibitors, the effect of valproic acid in combination with prostratin was analyzed. J-Lat6.3kRed2 cells were adjusted to $1 \times 10^6$ cells/ml. 80 µl cell aliquots were pipetted in a 96-well u-bottomed plate. Three-fold serial dilutions of 30, 10, and 3.3 mM valproic acid (VpA) were made by serial dilution in a 96-well v-bottomed plate and 10 µl of these dilutions, or medium alone was added to cells in final concentrations of 3 mM, 1 mM, 0.3 mM and 0 mM, respectively. Three-fold serial dilutions of 100, 33, 11, 3.7 µM prostratin were made in a 96-well v-bottomed plate and 10 µl of these dilutions, or medium alone was added to cells in final concentrations of 10 µM, 3.33 µM, 1.1 µM, 0.37 µM, and 0 µM, respectively. Samples were mixed by pipetting, returned to an incubator for 18 hours. HIV-LTR-driven expression of GFP was assessed by flow cytometry as described above. This experiment also showed that the histone deacetylase inhibitor, valproic acid, synergizes the effect prostratin has on the activation of latent HIV expression. For example, at a concentration of 0.3 mM, valproic acid potentiated the effect of prostratin (at 0.37 µM) about 6-7 fold. A representative result of this experiment is shown in FIG. 3.

Example 5

Administration Valproic Acid Reduces Prostratin-Induced Cell Death

Figure 4:
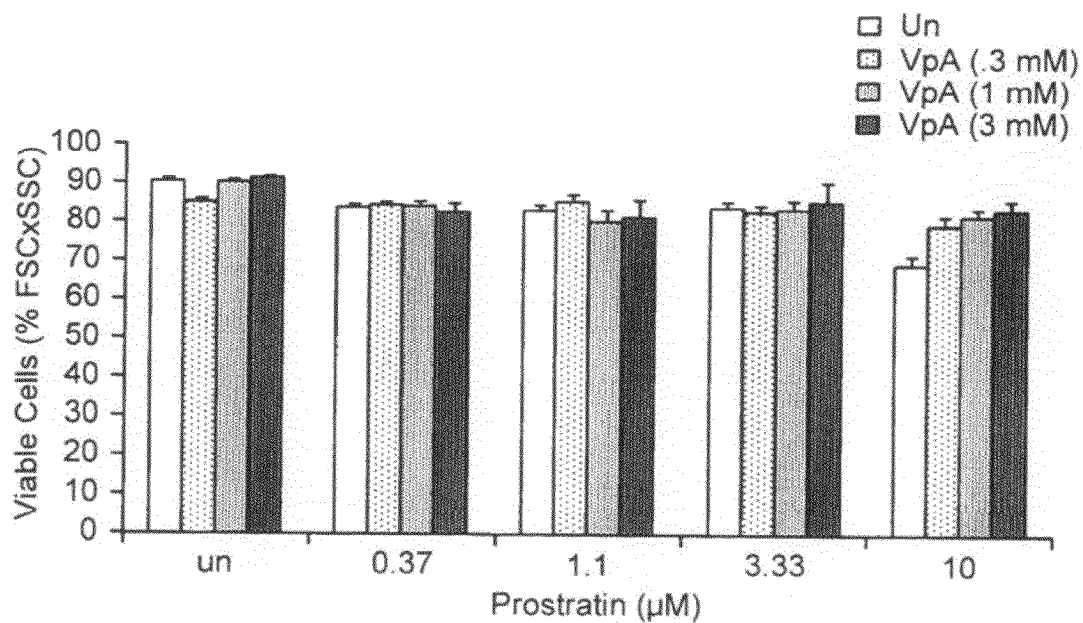
FIG. 4 shows that administration of valproic acid (VpA) reduces prostratin-induced cell death. Cell viability (expressed as viability (% FSC×SSC) was determined as in FIG. 2. VpA and prostratin were used at the concentrations indicated. Details are described in Example 5.

As described in Example 3 for TSA, the effect of valproic acid on blocking prostratin-induced cell death was analyzed using the same experimental set-up as described in Example 4. Although in this experiment the prostratin-induced cell death was less pronounced it was evident that at all tested concentrations, valproic acid blocked prostratin-induced cell death when prostratin was used at a concentration of 10 µM (FIG. 4)

Example 6

Tat Synergizes with TNF to Activate Expression of Latent HIV

To test whether the viral transcription activator protein, Tat, also has a synergistic effect on TNF mediated activation of latent HIV expression the following cell transfection experiment was performed. $10^6$ J-Lat 6.3 cells cultured in RPMI+ 10% fetal calf serum (FCS) and penicillin/streptomycin were pelleted by centrifugation and resuspended in 0.4 mL RPMI without serum. This cell suspension was mixed with 1 µg of pMACS-kk H2kk expression vector DNA (Miltenyi Biotech; see also Williams et al., 2006, *EMBO J* 25:139-149) encoding mouse cell surface-expressed MHC class I (Petry et al., 1999, *Int Immunol* 11:753-763; Tetsu and McCormick, 1999, *Nature* 398:422-426; Porter et al., 2002, *J Immunol* 168: 4936-4945; Finotto et al., 2001, *J Exp Med* 193: 1247-1260), and 10 µg of pCMV4 (Andersson et al., 1989, *J Biol Chem* 264 (14):8222-8229), or 10 µg pCMV4-FLAG-Tat expression vector (gift of Eric Verdin), transferred to a 0.4 cm gap electroporation cuvette (Stratagene), and electroporated at 975 µF, 250 mV for ~$25 \times 10^{-3}$ seconds. Electroporated cells were resuspended in 4 mL medium RPMI, supplemented with 10% fetal calf serum and penicillin/streptomycin and incubated for 48 hours at 37° C., 5% $CO_2$, 90% humidity. 90 µl aliquots of each sample were distributed to U-bottomed 96-well plates and 10 µl of 200 ng/mL TNF-α (Biosource), 10 µl of 1 mM Trichostatin A (Biomol), or 10 µl of RPMI (i.e., unstimulated cells) were added. For 30'-pulse TNF-α stimulation experiments, 10 µl of 200 ng/mL TNF-α was added to 90 µl cell suspension for 30 minutes.

After these treatments, the cells were transferred to a V-bottomed 96 well plate and centrifuged at 1,800 rpm for 3 minutes. The supernatant was removed and replaced, and procedure was repeated 2×. Cells were resuspended in 100 μl fresh RPMI with 10% serum and penicillin/streptomycin. 16 hours after treatment, cells were pelleted by centrifugation, and resuspended in 50 μl PBS+1:100 dilution of streptavidin-conjugated anti-H2kk antibody (BD Pharmingen). Samples were incubated 10 minutes, diluted in 200 μl PBS, pelleted by centrifugation, and supernatant removed. Cells were resuspended in 50 μl PBS+1:100 dilution of biotin-allophycoerythrin (APC), incubated 10 minutes, diluted in 200 μl PBS, pelleted by centrifugation, supernatant removed, resuspended in 100 μl PBS, pelleted by centrifugation, supernatant removed and resuspended in 50 μl PBS.

Figure 5:
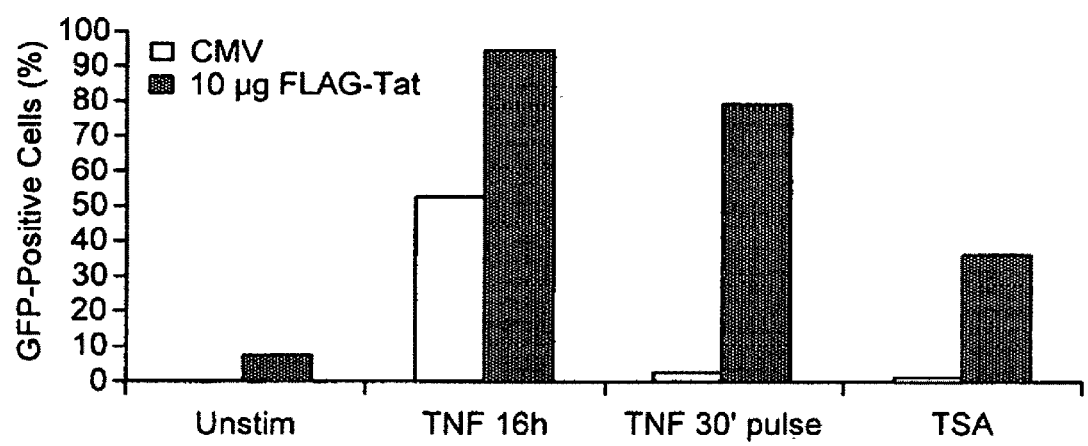
FIG. 5 shows that Tat synergizes with TNF or TSA to activate latent HIV expression in J-Lat 6.3 cells. Tat additionally synergizes with temporally limited induction of NF-κB by transient stimulation with TNF-α (30 minute-pulse followed by wash). HIV expression was determined as % of GFP-positive cells. J-Lat 6.3 cells were either transfected with an empty CMV expression plasmid (CMV) or with a CMV expression plasmid encoding FLAG-Tat (FLAG-Tat) as indicated. Unstim, unstimulated. Details are described in Example 6.

Cell samples were analyzed by flow cytometry using a Beckton Dickinson FACSCalibur. Cells were analyzed using FlowJo (TreeSoft) flow cytometry analysis software. Live cells were identified by characteristic light scatter and defraction and exclusively analyzed. Cells with APC fluorescence greater that untransfected cells stained with biotin-APC were considered to be Hak-positive, and to have been successfully transfected. Subsequent analyses were restricted to this subset of cells. Cells with greater GFP fluorescence than a non-GFP expressing Jurkat cell line were scored as GFP-positive. Percent GFP-positive cells was quantified and plotted. A representative result is shown in FIG. 5.

This experiment demonstrates synergistic activation of latent HIV expression with coadministration of Tat and TNF or TSA. Whereas Tat alone induced only a moderate level of latent HIV-driven expression of GFP, coadministration of either TNF or TSA strongly enhanced this activity (FIG. 5). Transient induction of NF-κB with 30-minute pulse treatment of TNF-α drove weak expression of latent HIV. However, expression of latent HIV in Tat-expressing cells was strongly sensitized to TNF-α pulse (FIG. 5). These data demonstrate the effectiveness of Tat as a synergistic agent with weak activators of HIV expression.

Example 7

Figure 6:
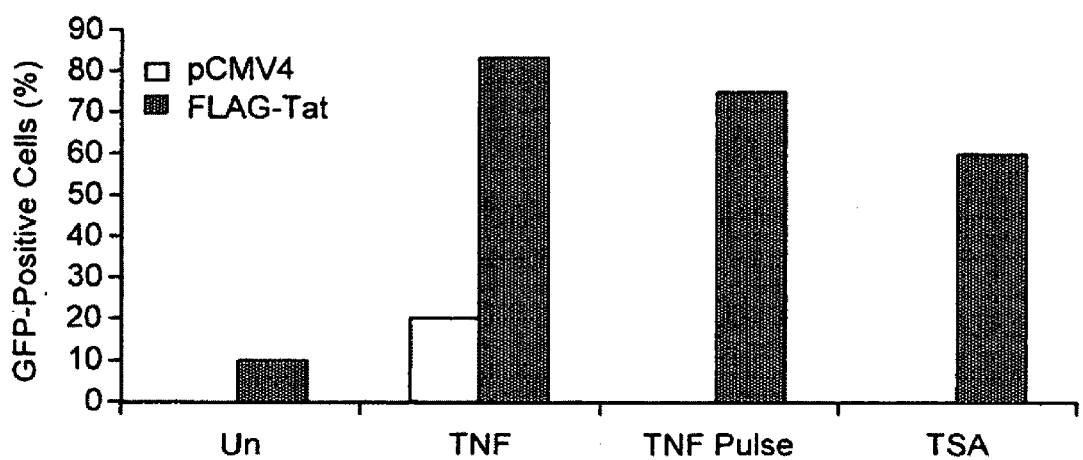
FIG. 6 shows that TNF or TSA synergizes with Tat to activate latent HIV expression in J-Lat 9.2 cells. Tat additionally synergizes with temporally limited induction of NF-κB by transient stimulation with TNF-α (30 minute-pulse followed by wash). HIV expression was determined as % of GFP-positive cells. J-Lat 6.3 cells were either transfected with an empty CMV expression plasmid (CMV) or with a CMV expression plasmid encoding FLAG-Tat (FLAG-Tat) as indicated. Unstim, unstimulated. Details are described in Example 6.

TNF and TSA Synergizes with Tat to Activate Expression of Latent HIV in J-Lat 9.2 Cells The experiment described in Example 6 using J-Lat 6.3 cells was repeated using J-Lat 9.2 cells. A similar result was obtained (FIG. 6).

What is claimed is:

1. A method for activating latent HIV expression in a mammalian cell having an integrated HIV genome, the method comprising the steps of:
   (a) contacting the mammalian cell with an amount of an activator of latent HIV expression selected from the group consisting of prostratin, DPP, and structural analogs thereof and effective to activate latent HIV expression to a first expression level; and
   (b) contacting the mammalian cell with an amount of an inhibitor of histone deacetylase effective to activate latent HIV expression to a second expression level, wherein the activator of latent HIV expression and the inhibitor of histone deacetylase synergize to generate the second expression level;
   wherein a cytotoxic effect in the mammalian cell caused by the amount of activator of latent HIV expression in the presence of the inhibitor of histone deacetylase is less than the cytotoxic effect in the mammalian cell caused by the amount of the activator of latent HIV expression in the absence of the inhibitor of histone deacetylase.

2. The method of claim 1, wherein the activator of latent HIV expression is prostratin.

3. The method of claim 1, wherein the inhibitor of histone deacetylase is selected from the group consisting of trichostatin A, valproic acid, sodium butyrate, and structural analogs thereof.

4. The method of claim 3, wherein the inhibitor of histone deacetylase is trichostatin A.

5. The method of claim 3, wherein the inhibitor of histone deacetylase is valproic acid.

6. The method of claim 3, wherein the inhibitor of histone deacetylase is sodium butyrate.

7. The method of claim 1, wherein the activator of latent HIV expression is prostratin and the inhibitor of histone deacetylase is trichostatin A.

8. The method of claim 7, wherein the amount of prostratin contacting the mammalian cell is less than 10% of an amount of prostratin that is required to obtain the second expression level in the absence of trichostatin A.

9. The method of claim 1, wherein the mammalian cell is in a human.

10. The method of claim 9, further comprising the step of:
    (c) administering HAART.

11. The method of claim 9, further comprising the step of:
    (c) administering an immunotoxin.

12. The method of claim 1, further comprising the step of:
    (c) administering a Tat.

13. The method of claim 1, wherein the mammalian cell is a resting lymphoid mononuclear cell.

14. The method of claim 13, wherein the resting lymphoid mononuclear cell is a $CD4^+$ T cell.

15. The method of claim 1, wherein the mammalian cell is a myeloid mononuclear cell or a tissue macrophage.

16. The method of claim 15, wherein the myeloid mononuclear cell is a peripheral blood mononuclear cell.

17. The method of claim 1, wherein the inhibitor of histone deacetylase is selected from the group consisting of butyric acid, phenylbutyrate, phenylacetate, trapoxin B, MS 275-27, a hydroximate, depudecin, oxamflatin, apicidin, Scriptaid, pyroxamide, 2-amino-8-oxo-9,10-epoxy-decanoyl, 3-(4-aroyl-1H-pyrrol-2-yl)-N-hydroxy-2-propenamide, CI-994, CHAP1, CHAP31, CHAP50, MS-275, M344, LAQ-824, FK228, FR901228, HC-toxin, and structural analogs thereof, wherein the hydroximate is selected from the group consisting of suberoylanilide hydroxamic acid (SAHA), azelaic bishydroxamic acid (ABHA), suberic bishydroxamic acid (SBHA), and m-carboxycinnamic acid bis-hydroxamide (CBHA).

18. A method for activating latent HIV expression in a mammalian cell having an integrated HIV genome, the method comprising the steps of:
    (a) contacting the mammalian cell with an amount of an activator of latent HIV expression selected from the group consisting of prostratin, DPP, and structural analogs thereof and effective to activate latent HIV expression to a first expression level;
    (b) contacting the mammalian cell with an amount of an inhibitor of histone deacetylase effective to activate latent HIV expression to a second expression level, wherein the activator of latent HIV expression and the inhibitor of histone deacetylase synergize to generate the second expression level; and
    (c) determining the second expression level, wherein a cytotoxic effect in the mammalian cell caused by the amount of activator of latent HIV expression in the presence of the inhibitor of histone deacetylase is less than the cytotoxic effect in the mammalian cell caused by the amount of the activator of latent HIV expression in the absence of the inhibitor of histone deacetylase.

19. The method of claim 18, wherein the activator of latent HIV expression is prostratin.

20. The method of claim 18, wherein the inhibitor of histone deacetylase is selected from the group consisting of trichostatin A, valproic acid, sodium butyrate, and structural analogs thereof.

21. The method of claim 20, wherein the inhibitor of histone deacetylase is trichostatin A.

22. The method of claim 20, wherein the inhibitor of histone deacetylase is valproic acid.

23. The method of claim 20, wherein the inhibitor of histone deacetylase is sodium butyrate.

24. The method of claim 18, wherein the activator of latent HIV expression is prostratin and the inhibitor of histone deacetylase is trichostatin A.

25. The method of claim 24, wherein the amount of prostratin contacting the mammalian cell is less than 10% of an amount of prostratin that is required to obtain the second expression level in the absence of trichostatin A.

26. The method of claim 25, wherein the mammalian cell is in a human.

27. The method of claim 26, further comprising the step of:
(d) administering HAART.

28. The method of claim 26, further comprising the step of:
(d) administering an immunotoxin.

29. The method of claim 18, further comprising the step of:
(d) administering a Tat.

30. The method of claim 18, wherein the mammalian cell is a resting lymphoid mononuclear cell.

31. The method of claim 30, wherein the resting lymphoid mononuclear cell is a $CD4^+$ T cell.

32. The method of claim 18, wherein the mammalian cell is a myeloid mononuclear cell or a tissue macrophage.

33. The method of claim 32, wherein the myeloid mononuclear cell is a peripheral blood mononuclear cell.

34. The method of claim 18, wherein the inhibitor of histone deacetylase is selected from the group consisting of butyric acid, phenylbutyrate, phenylacetate, trapoxin B, MS 275-27, a hydroximate, depudecin, oxamflatin, apicidin, Scriptaid, pyroxamide, 2-amino-8-oxo-9,10-epoxy-decanoyl, 3-(4-aroyl-1H-pyrrol-2-yl)-N-hydroxy-2-propenamide, Cl-994, CHAP1, CHAP31, CHAP50, MS-275, M344, LAQ-824, FK228, FR901228, HC-toxin, and structural analogs thereof,
wherein the hydroximate is selected from the group consisting of suberoylanilide hydroxamic acid (SAHA), azelaic bishydroxamic acid (ABHA), suberic bishydroxamic acid (SBHA), and m-carboxycinnamic acid bis-hydroxamide (CBHA).

* * * * *

UNITED STATES PATENT AND TRADEMARK OFFICE
CERTIFICATE OF CORRECTION

| | | |
|---|---|---|
| PATENT NO. | : 8,247,613 B2 | Page 1 of 1 |
| APPLICATION NO. | : 12/297034 | |
| DATED | : August 21, 2012 | |
| INVENTOR(S) | : Samuel A. F. Williams et al. | |

It is certified that error appears in the above-identified patent and that said Letters Patent is hereby corrected as shown below:

In column 37, line 28, please delete "25" and insert --18--.

Signed and Sealed this
Second Day of April, 2013

Teresa Stanek Rea
*Acting Director of the United States Patent and Trademark Office*